US008658652B2

(12) United States Patent
Roberts et al.

(10) Patent No.: US 8,658,652 B2
(45) Date of Patent: Feb. 25, 2014

(54) ANTIFOLATE COMBINATIONS

(75) Inventors: Michael J. Roberts, Charlotte, NC (US); Gerry Rowse, Waxhaw, NC (US)

(73) Assignee: Chelsea Therapeutics, Inc., Charlotte, NC (US)

( * ) Notice: Subject to any disclaimer, the term of this patent is extended or adjusted under 35 U.S.C. 154(b) by 0 days.

(21) Appl. No.: 13/313,116

(22) Filed: Dec. 7, 2011

(65) Prior Publication Data

US 2012/0142692 A1    Jun. 7, 2012

Related U.S. Application Data

(60) Provisional application No. 61/420,528, filed on Dec. 7, 2010.

(51) Int. Cl.
*A61K 31/517* (2006.01)
*A61K 31/519* (2006.01)
*A61P 19/02* (2006.01)
*A61P 29/00* (2006.01)

(52) U.S. Cl.
USPC ........ 514/258.1; 514/249; 544/283; 544/291; 544/257

(58) Field of Classification Search
USPC ................ 514/258.1, 249; 544/283, 291, 257
See application file for complete search history.

(56) References Cited

U.S. PATENT DOCUMENTS

| | | | |
|---|---|---|---|
| 4,818,753 | A | 4/1989 | Colwell et al. |
| 4,996,206 | A | 2/1991 | Taylor et al. |
| 4,996,207 | A | 2/1991 | Nair et al. |
| 5,028,608 | A | 7/1991 | Taylor et al. |
| 5,073,554 | A | 12/1991 | Nair |
| 5,106,974 | A | 4/1992 | Akimoto et al. |
| 5,248,775 | A | 9/1993 | Taylor et al. |
| 5,344,932 | A | 9/1994 | Taylor |
| 5,534,518 | A | 7/1996 | Henrie, II et al. |
| 5,550,128 | A | 8/1996 | Nair et al. |
| 5,593,999 | A | 1/1997 | Nair et al. |
| 5,866,580 | A | 2/1999 | Gangjee |
| 5,912,251 | A | 6/1999 | Nair |
| 6,048,736 | A | 4/2000 | Kosak |
| 6,667,318 | B2 | 12/2003 | Burdick et al. |
| 7,060,825 | B2 | 6/2006 | Wu et al. |
| 7,612,071 | B2 | 11/2009 | Kamen et al. |
| 2001/0034333 | A1 | 10/2001 | Kosak |
| 2002/0077280 | A1 | 6/2002 | Judice et al. |
| 2002/0081455 | A1 | 6/2002 | Lee |
| 2003/0162721 | A1 | 8/2003 | Mehlem |
| 2003/0181635 | A1 | 9/2003 | Kochat et al. |
| 2004/0092739 | A1 | 5/2004 | Xiao et al. |
| 2005/0020833 | A1 | 1/2005 | Wu et al. |
| 2006/0111272 | A1 | 5/2006 | Roberts et al. |
| 2006/0160751 | A1 | 7/2006 | McGuire |
| 2009/0253719 | A1 | 10/2009 | Pimplaskar et al. |
| 2009/0253720 | A1 | 10/2009 | Roberts et al. |
| 2011/0081338 | A1* | 4/2011 | Roberts et al. ............. 424/133.1 |
| 2011/0082149 | A1* | 4/2011 | Roberts et al. ................ 514/249 |
| 2011/0124650 | A1* | 5/2011 | Pimplaskar et al. .......... 514/249 |
| 2011/0237609 | A1 | 9/2011 | Pimplaskar |

FOREIGN PATENT DOCUMENTS

| | | |
|---|---|---|
| EP | 0 239 362 | 9/1987 |
| EP | 0 340 905 | 11/1989 |
| WO | WO 93/13079 | 7/1993 |
| WO | WO 02/081455 A1 | 10/2002 |
| WO | WO 2009/126637 | 10/2009 |
| WO | WO 2011/005832 | 1/2011 |
| WO | WO 2011/056957 | 5/2011 |

OTHER PUBLICATIONS

Chou T.C. Cancer Res. 2010, 70 (2), 440-446.*
www.clinicaltrials.gov/archive/NCT01116141/2010_10_13, "A Study of CH-4051 in Patients with Rheumatoid Arthritis (RA)."
Morgan et al., "Folate Supplementation During Methotrexate Therapy for Rheumatoid Arthritis," *Clinical and Experimental Rheumatology*, 2010, pp. S102-S109, vol. 28, No. 5, Suppl. 61.
Abraham et al., "Folate Analogues. 34. Synthesis and Antitumor Activity of Non-Polyglutamylatable Inhibitors of Dihydrofolate Reductase," *J. Med. Chem.*, 1991, vol. 34, pp. 222-227.
Abraham et al., "Aldehyde Oxidase Mediated 7-Hydroxylation of Antifolates and Its Therapeutic Relevance," *Cellular Pharmacology*, 1996, vol. 3, pp. 29-34.
Alarcon et al., "Controlled Trial of Methotrexate Versus 10-Deazaaminopterin in the Treatment of Rheumatoid Arthristis," *Arthritis Rheumatism*, 1992, pp. 600-660, vol. 51, No. 5.
Amato et al., "Metabolism-Based Antifolate Drug Design: MDAM and MTREX," *Pharmacology and Therapeutics in the New Millennium*, 2001, pp. 204-212, Narosa Publishing House, New Delhi, India.
Baggott et al., "Folylpoly-γ-glutamates as Cosubstrates of 10-Formyltetrandrofolate:5'-Phosphoribosyl-5amino-4-imidazole-Carboxamide Formyltransferase," *Biochemistry*, 1979, pp. 1036-1041, vol. 18, No. 1.
Baugh et al., "Polygammaglutamyl Metabolites of Methotrexate," *Biochemical and Biophysical Research Communications*, 1973, pp. 27-34, vol. 52, No. 1.
Blakley, *The Biochemistry of Folic Acid and Related Pteridines*. 1969, Amsterdam Elsevier. [Book].
Broxterman et al., "Cancer Research 2001: Drug Resistance, New Targets and Drug Combinations," *Drug Resistance Updates*, 2001, vol. 4, pp. 197-209.

(Continued)

*Primary Examiner* — Sreeni Padmanabhan
*Assistant Examiner* — Irina Neagu
(74) *Attorney, Agent, or Firm* — Womble Carlyle Sandridge & Rice, LLP

(57) ABSTRACT

The present invention provides combinations of active agents, such combinations comprising one or more antifolate compounds. The particularly can include methotrexate and one or more further antifolate compounds. In specific embodiments, the combinations are useful for treating certain conditions, such as rheumatoid arthritis. The invention also provides articles useful to provide the combinations in desirable dosage forms and combinations. The combinations further may be useful in the treatment of further conditions, including abnormal cell proliferation, inflammatory diseases, asthma, and arthritis.

22 Claims, 11 Drawing Sheets

(56) References Cited

OTHER PUBLICATIONS

Bryant et al., "Metabolism-Blocked Antifolate-2," *Proc. Am. Assoc. Cancer Res.*, 1999, vol. 40, p. 293 (Abstract No. 1944).

Caira, "Crystalline Polymorphism of Organic Compounds," *Topics in Current Chemistry*, 1998, pp. 163-208, vol. 198.

Caperelli et al., "The Human Glycinamide Ribonucleotide Transformylase Domain: Purification, Characterization and Kinetic Mechanism," *Archives of Biochemistry and Biophysics*, 1997, pp. 98-103, vol. 341, No. 1.

Castaneda et al., "Controlled Trial of Methotrexate Versus CH-1504 in the Treatment of Rheumatoid Arthritis," *Journal of Rheumatology*, 2006, pp. 862-864, vol. 33, No. 1.

Choi et al., "Methotrexate and Mortality in Patients with Rheumatoid Arthritis: A Prospective Study", *The Lancet*, 2002, pp. 1173-1177, vol. 359.

Clowes et al., "Prevention of Stenosis After Vascular Reconstruction: Pharmacologic Control of Intimal Hyperplasia—A Review," *Journal of Vascular Surgery*, 1991, pp. 885-890, vol. 13.

Degraw et al., "Synthesis and Antifolate Activity of 8,10-Dideazaminopterin," *J. Het. Chem.*, 1982, vol. 19, pp. 1587-1588.

Dessein et al., "Effects of Disease Modifying Agents and Dietary Intervention on Insulin Resistance and Dyslipidemia in Inflammatory Arthritis: A Pilot Study," *Arthritis Res.* 2002, pp. 1-7, vol. 4, No. 6.

Dolnick et al., "Human Thymidylate Synthetase Derived From Blast Cells of Patients With Acute Myelocytic Leukemia," The Journal of Biological Chemistry, 1977, pp. 7697-7703, vol. 252, No. 1.

Gahtan et al., "Inflammatory Pathogenesis in Alzheimer's Disease: Biological Mechanisms and Cognitive Sequeli," *Neuroscience and Biobehavioral Reviews*, 1999, pp. 615-633, vol. 23, No. 5.

Gangjee et al., "Effect of N-9-Methylation and Bridge Atom Variation on the Activity of 5-Substituted 2, 4-Diaminopyrrolo (2,3-d) Pyrimidines Against Dihydrofolate Reductases From *Pneumocystis carinii* and *Toxoplasma gondii*," *Journal of Medicinal Chemistry*, 1997, pp. 1173-1177, vol. 40, No. 7.

Gangjee et al., "Nonclassical 2,4-Diamino-8-Deazafolate Analogues as Inhibitors of Dihydrofolate Reductases from Rat Liver, *Pneumocystis carinii*, and *Toxoplasma gondii*," *J. Med. Chem.*, 1996, vol. 39(9), pp. 1836-1845.

Gangjee et al., "Design, Synthesis, and Biological Activities of Classical N-{4-[2-(2-Amino-4-ethylpyrrolo[2,3-*d*]pyrimidin-5-yl)ethyl]benzoyl}-L-glutamic Acid and Its 6-Methyl Derivative as Potential Dual Inhibitors of Thymidylate Synthase and Dihydrofolate Reductase and as Potential Antitumor Agents," *J. Med. Chem..*, 2003, pp. 591-600, vol. 46, No. 4.

Grant Proposal, "Mobiletrex (M-Trex) for the Prevention and/or Treatment of Coronary Heart Disease", American Heart Association, Jan. 23, 2003, 35 pages.

Grant Application, "Anti-inflammatory Antifolate Therapy for Heart Disease", Department of Health and Human Services, Jan. 23, 2003, 27 pages.

Gupta et al., "Inflammation and Alzheimer's Disease," *The International Journal of Clinical Practice*, 2003, pp. 36-39, vol. 57, No. 1.

Itoh et al., "Non-Glutamate Type Pyrrolo[2,2-*d*]pyrimidine Antifolates. II. Synthesis and Antitumor Activity of N-Substituted Glutamine Analogs," *Chemical and Pharmaceutical Bulletin, Pharmaceutical Society of Japan*, 1996, pp. 1498-1509, vol. 44, No. 8.

Jackman, "Antifolate Drugs in Cancer Therapy," *Book Review: Reprints from Current Trends, Drug Discovery Today*, 1999.

Johns et al., "Enzymic Oxidation of Methotrexiate and Aminopterin," *Life Sciences*, 1964, pp. 1383-1388, vol. 3.

Johns et al.,"Metabolism of Folate Antagonists," *Annals New York Academy of Sciences*, 1971, pp. 378-386, vol. 186.

Kisliuk, "Deaza Analogs of Folic Acid as Antitumor Agents," *Current Pharmaceutical Design*, 2003, vol. 9(31), pp. 2615-2625.

Kormeili et al., Psoriasis: Immunopathogenesis and Evolving Immunomodulators and Systemic Therapies; U.S. Experiences, *British Journal of Dermatology*, 2004, pp. 3-15, vol. 151, No. 1.

Lemanske, "Inflammation in Childhood Asthma and Other Wheezing Disorders," *Pediatrics*, 2002, pp. 368-372, vol. 109, No. 2.

Lim, et al., "Gene-Nutrient Interactions Among Determinants of Folate and One-Carbon Metabolism on the Risk of Non-Hodgkin Lymphoma: NCI-SEER Case-Control Study," *Blood*, 2007, pp. 3050-3059, vol. 109, No. 7.

Lind, "Circulating Markers of Inflammation and Atherosclerosis," *Atherosclerosis*, 2003, pp. 203-214, vol. 169, No. 2.

Lloyd et al., "Crystallization and Preliminary Crystallographic Analysis of Carboxypeptidase $G_2$ From *Pseudomonas* sp. Strain RS-16," *J. Mol. Biol.*, 1991, pp. 17-18, vol. 220.

Matherly et al., "Membrane Transport of Folates," *Vitam Horm*, 2003, pp. 403-456, vol. 66.

McCullough et al., "Purification and Properties of Carboxypeptidase G" *The Journal of Biological Chemistry*, 1971, pp. 7201-7213, vol. 246, No. 23.

McGuire et al., "Enzymatic Synthesis of Polyglutamate Derivatives of 7-Hydroxymethotrexate!," *Biochemical Pharmacology*, 1984, pp. 1355-1361, vol. 33, No. 8.

McGuire et al., "Biochemical and Growth Inhibitory Effects of the *erythro* and *threo* Isomers of γ-Fluoromethotrexate, a Methotrexate Analogue Defective in Polyglutamylation," *Cancer Research*, 1989, pp. 4517-4525, vol. 49, No. 12.

McGuire et al., "Biochemical and Growth Inhibition Studies of Methotrexate and Aminopterin Analogues Containing a Tetrazole Ring in Place of the γCarboxyl Group," *Cancer Research*, 1990, pp. 1726-1731, vol. 50.

McGuire et al., "Biochemical and Biological Properties of Methotrexate Analogs Containing D-glutamic Acid or D-erythro,threo-4-fluoroglutamic Acid," *Biochemical Pharmacology*, 1991, pp. 2400-2403, vol. 42, No. 12.

McGuire et al., "Novel 6,5-fused Ring Heterocyclic Antifolates: Biochemical and Biological Characterization," *Cancer Research*, 1994, pp. 2673-2679, vol. 54.

McGuire, "Anticancer Antifolates: Current Status and Future Directions," *Current Pharmaceutical Design*, 2003, vol. 9(31), pp. 2593-2613.

McGuire et al., "5-Amino-4-Imidazolecarboxamide Riboside Potentiates Both Transport of Reduced Folates and Antifolates by the Human Reduced Folate Carrier and Their Subsequent Metabolism," *Cancer Research*, 2006, pp. 3836-3844, vol. 66, No. 7.

McGuire, et al., "Metabolism-blocked Antifolates as Potential Antirheumatoid Arthritis Agents: 4-Amino-4-deoxy-5,8,10-trideazapteroyl-D,L-4'-methyleneglutamic Acid (CH-1504) and Its Analogs," *Biochemical Pharmacology*, 2009, pp. 1161-1172, vol. 77, No. 7.

Merriam-Webster's Collegiate Dictionary, Merriam-Webster Incorporated: Springfield, Massachusetts, 1993, pp. 311 and 996.

Mirza et al., "The Absence of Reactive Astrocytosis in Indicative of a Unique Inflammatory Process in Parkinson's Disease," *Neuroscience*, 2000, pp. 425-432, vol. 95, No. 2.

Miwa et al., "A Novel Synthetic Approach to Pyrrolo(2,3-d)pyrimidine Antifolates," *Journal of Organic Chemistry*, 1993, pp. 1696-1701, vol. 58, No. 7.

Montgomery et al., "Design and Synthesis of Folate Analogs as Antimetabolites in Folate Antagonists as Therapeutic Agents," *Biochemistry, Molecular Actions and Synthetic Designs*, 1984, pp. 219-261, vol. 1.

Moran et al. "Relative Substrate Activities of Structurally Related Pteridine, Quinazoline, and Pyrimidine Analogs for Mouse Liver Folylpolyglutamate Synthetase," *Molecular Pharmacology*, 1989, pp. 736-743, vol. 36, No. 5.

Morissette et al., "High-Throughput Crystallization: Polymorphs, Salts, Co-Crystals and Solvates of Pharmaceutical Solids," *Advance Drug Delivery Reviews*, 2004, pp. 275-300, vol. 56.

Nagayama et al., "Eosinophils and Basophilic Cells in Sputum and Nasal Smears Taken from Infants and Young Children during Acute Asthma," *Pediatr. Allergy Immunol.*, 1995, vol. 6, pp. 204-208.

Nair et al., "Folate Analogues. 34. Synthesis and Antitumor Activity of Non-Polyglutamylatable Inhibitors of Dihydrofolate Reductase," *J. Med. Chem*, 1991, pp. 222-227, vol. 34.

Nair et al., "Polyglutamylation as a Determinant of Cytotoxicity of Classical Folate Analogue Inhibitors of Thymidylate Synthase and Glycinamide Ribonucleotide Formyltransferase," *Cellular Pharmacology*, 1994, vol. 1, pp. 245-249.

(56) References Cited

OTHER PUBLICATIONS

Nair et al., "Aldehyde Oxidase Mediated 7-Hydroxylation of Antifolates and its Therapeutic Relevance," *Cellular Pharmacology*, 1996, pp. 29-34, vol. 3.

Nair et al., "Metabolism-Blocked Antifolates-1," *Proc. Am. Assoc. Cancer Res.*, 1998, vol. 39, p. 431 (Abstract No. 2938).

Nair et al., "Metabolism Blocked Classical Folate Analog Inhibitors of Dihydrofolate Reductase-1: Synthesis and Biological Evaluation of Mobiletrex," *Medicinal Chemistry Research*, 1999, pp. 176-185, vol. 9, No. 3.

Nair et al., "Metabolism-Blocked Antifolates, 3: Enantiomers of 4'methylene-5,8,10-Trideazaaminopterin (M-Trex)," *Proceedings of the American Association for Cancer Research Annual Meeting*, 2001, pp. 294, vol. 42. (Abstract No. 1583).

Pauwels et al. "Burden and Clinical Features of Chronic Obstructive Pulmonary Disease (COPD)," *R A. Lancet* (2004) 364(9434):613-20).

Park et al., "Effects of Antirheumatic Therapy on Serum Lipid Levels in Patients with Rheumatoid Arthritis: A Prospective Study", Am. J. Med., 2002, pp. 188-193, vol. 113, No. 3.

Renouard et al., "Functionalized Tetradentate Ligands for Ru-Sensitized Solar Cells," *Tetrahedron*, 2001, vol. 57, pp. 8145-8150.

Rosowsky et al., "Analogues of Methotrexate and Aminopterin with γ-Methylene and γ-Cyano Substitution of the Glutamate Side Chain: Synthesis and in Vitro Biological Activity," *J. Med. Chem.*, 1991, vol. 34, pp. 203-208.

Ross, "Atherosclerosis—An Inflammatory Disease," *New England Journal of Medicine*, 1999, pp. 115-126, vol. 340.

Sherwood et al., "Purification and Properties of Carboxypeptidase G2 From *Pseudomonas* sp. Strain RS-16," *Eur. J. Biochem.*, 1985, pp. 447-453, vol. 148.

Shilai et al., "Selective Metallation of Thiophene and Thiazole Rings with Magnesium Amide Base," *J. Chem. Soc., Perkin Trans. 1*, 2001, pp. 442-444.

Takimoto, "New Antifolates: Pharmacology and Clinical Applications," *The Oncologist*, 1996, pp. 68-81, vol. 1.

Van Triest et al., "Downstream Molecular Determinants of Response to 5-Fluorouracil and Antifolate Thymidylate Synthase Inhibitors," *Annals of Oncology*, 2000, pp. 385-391, vol. 11.

Wang et al. Review of Excipients and pH's for Parenteral Products Used in the United States, (1980) *J. Parent. Drug Assn.* 34(6):452-462.

West, "Solid State Chemistry and its Applications," Wiley, New York, 1988, pp. 358 and 365.

Yan et al., "Folic Acid Analogs . III. N-(2-[2-(,4-diamino-6-quinazolinyl)ethyl] benzoyl)-L-glutamic acid," *J. Heterocyclic Chem.*, 1979, 541-544, vol. 16.

\* cited by examiner

ANTIFOLATE COMBINATIONS

CROSS REFERENCE TO RELATED APPLICATIONS

The present application claims priority to U.S. Provisional Patent Application No. 61/420,528, filed Dec. 7, 2010, the disclosure of which is incorporated herein by reference in its entirety.

FIELD OF THE INVENTION

The present application is directed to combinations of two or more active compounds. More specifically, the active agent combinations can comprise two or more specific antifolate compounds.

BACKGROUND

Folic acid is a water-soluble B vitamin known by the systematic name N-[4(2-amino-4-hydroxy-pteridin-6-ylmethylamino)-benzoyl]-L(+)-glutamic acid and having the structure provided below in Formula (1).

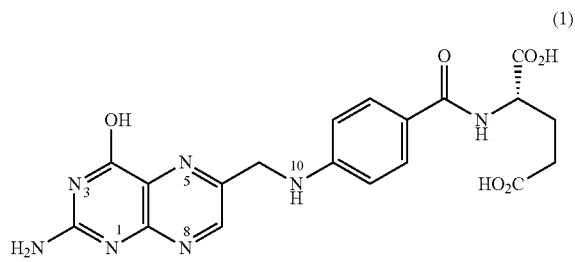 [SMILES: Nc1nc(O)c2nc(CNc3ccc(C(=O)N[C@@H](CCC(=O)O)C(=O)O)cc3)cnc2n1]

As seen in Formula (1), the folic acid structure can generally be described as being formed of a pteridine ring, a para-aminobenzoic acid moiety, and a glutamate moiety. Folic acid and its derivatives are necessary for metabolism and growth, particularly participating in the body's synthesis of thymidylate, amino acids, and purines. Derivatives of folic acid, such as naturally occurring folates, are known to have biochemical effects comparable to folic acid. Folic acid is known to be derivatized via hydrogenation, such as at the 1,4-diazine ring, or being methylated, formaldehydylated, or bridged, wherein substitution is generally at the $N^5$ or $N^{10}$ positions. Folates have been studied for efficacy in various uses including reduction in severity or incidence of birth defects, heart disease, stroke, memory loss, and age-related dementia.

Antifolate compounds, like folates, are structurally similar to folic acid; however, antifolate compounds function to disrupt folic acid metabolism. A review of antifolates is provided by Takamoto (1996) *The Oncologist*, 1:68-81, which is incorporated herein by reference. One specific group of antifolates, the so-called "classical antifolates," is characterized by the presence of a folic acid p-aminobenzoylglutamic acid side chain, or a derivative of that side chain. Another group of antifolates, the so-called "nonclassical antifolates," are characterized by the specific absence of the p-aminobenzoyl-glutamic group. Because antifolates have a physiological effect that is opposite the effect of folic acid, antifolates have been shown to exhibit useful physiological functions, such as the ability to destroy cancer cells by causing apoptosis.

Folate monoglutamylates and antifolate monoglutamylates are transported through cell membranes either in reduced form or unreduced form by carriers specific to those respective forms. Expression of these transport systems varies with cell type and cell growth conditions. After entering cells most folates, and many antifolates, are modified by polyglutamylation, wherein one glutamate residue is linked to a second glutamate residue at the α carboxy group via a peptide bond. This leads to formation of poly-L-γ-glutamylates, usually by addition of three to six glutamate residues. Enzymes that act on folates have a higher affinity for the polyglutamylated forms. Polyglutamylated folates generally exhibit a longer retention time within the cell.

An intact folate enzyme pathway is important to maintain de novo synthesis of the building blocks of DNA, as well as many important amino acids. Antifolate targets include the various enzymes involved in folate metabolism, including (i) dihydrofolate reductase (DHFR); (ii) thymidylate synthase (TS); (iii) folylpolyglutamyl synthase; and (iv) glycinamide ribonucleotide transformylase (GARFT) and aminoimidazole carboxamide ribonucleotide transformylase (AICART).

The reduced folate carrier (RFC), which is a transmembrane glycoprotein, plays an active role in the folate pathway transporting reduced folate into mammalian cells via the carrier mediated mechanism (as opposed to the receptor mediated mechanism). The RFC also transports antifolates, such as methotrexate. Thus, altering the ability of RFC to function can affect the ability of cells to uptake reduced folates.

Polyglutamylated folates can function as enzyme cofactors, whereas polyglutamylated antifolates generally function as enzyme inhibitors. Moreover, interference with folate metabolism prevents de novo synthesis of DNA and some amino acids, thereby enabling antifolate selective cytotoxicity. Methotrexate, the structure of which is provided in Formula (2), is one antifolate that has shown use in treating conditions, such as cancer.

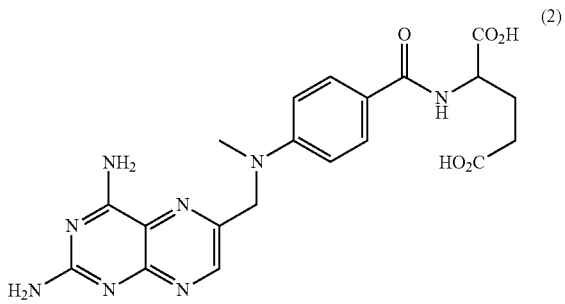 [SMILES: CN(Cc1cnc2nc(N)nc(N)c2n1)c1ccc(C(=O)NC(CCC(=O)O)C(=O)O)cc1]

Nair et al. (*J. Med. Chem.* (1991) 34:222-227), incorporated herein by reference, demonstrated that polyglutamylation of classical antifolates was not essential for anti-tumor activity and may even be undesirable in that polyglutamylation can lead to a loss of drug pharmacological activity and target specificity. This was followed by the discovery of numerous nonpolyglutamylatable classical antifolates. See Nair et al. (1998) *Proc. Amer. Assoc. Cancer Research* 39:431, which is incorporated herein by reference. One particular group of nonpolyglutamylatable antifolates are characterized by a methylidene group (i.e., a $=CH_2$ substituent) at the 4-position of the glutamate moiety. The presence of this chemical group has been shown to affect biological activity of the antifolate compound. See Nair et al. (1996) *Cellular Pharmacology* 3:29, which is incorporated herein by reference.

Further folic acid derivatives have also been studied in the search for antifolates with increased metabolic stability allowing for smaller doses and less frequent patient administration. For example, a dideaza (i.e., quinazoline-based) analog has been shown to avoid physiological hydroxylation on the pteridine ring system. Furthermore, replacement of the secondary amine nitrogen atom with an optionally substituted carbon atom has been shown to protect neighboring bonds from physiological cleavage.

One example of an antifolate having carbon replacement of the secondary amine nitrogen is 4-amino-4-deoxy-10-deazapteroyl-γ-methyleneglutamic acid—more commonly referred to as MDAM—the structure of which is provided in Formula (3).

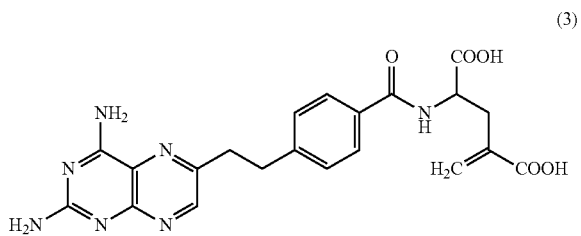 [SMILES: C=C(CC(NC(=O)c1ccc(CCc2cnc3nc(N)nc(N)c3n2)cc1)C(=O)O)C(=O)O]

(3)

The L-enantiomer of MDAM has been shown to exhibit increased physiological activity. See U.S. Pat. No. 5,550,128, which is incorporated herein by reference. Another example of a classical antifolate designed for metabolic stability is ZD1694, which is shown in Formula (4).

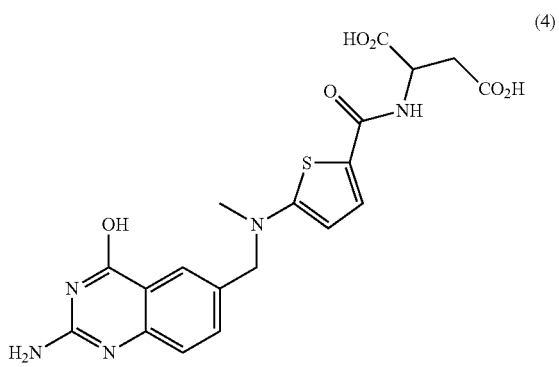 [SMILES: CN(Cc1ccc2nc(N)nc(O)c2c1)c1ccc(C(=O)NC(CC(=O)O)C(=O)O)s1]

(4)

A group of antifolate compounds according to the structure shown in Formula (5) combines several of the molecular features described above, and this group of compounds is known by the names MobileTrexate, MobileTrex, Mobiltrex, or M-Trex.

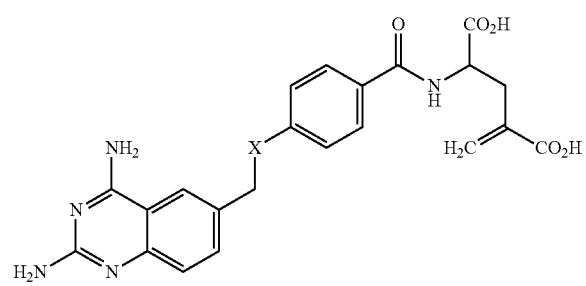

(5)

As shown in Formula (5), this group of compounds encompasses M-Trex, wherein X can be $CH_2$, $CHCH_3$, $CH(CH_2CH_3)$, NH, or $NCH_3$. Further antifolate compounds are disclosed in U.S. Pat. No. 7,951,812.

The effectiveness of antifolates arises from other factors in addition to metabolic inertness, as described above. The multiple enzymes involved in folic acid metabolism within the body present a choice of inhibition targets for antifolates. In other words, it is possible for antifolates to vary as to which enzyme(s) they inhibit. For example, some antifolates inhibit primarily dihydrofolate reductase (DHFR), while other antifolates inhibit primarily thymidylate synthase (TS), glycinamide ribonucleotide formyltransferase (GARFT), or aminoimidazole carboxamide ribonucleotide transformylase, while still other antifolates inhibit combinations of these enzymes.

In light of the usefulness of antifolates in treating a variety of conditions, there remains a need in the art for further applications of antifolates to treatment of specific conditions, including identifying combinations of antifolates with other active agents, including other antifolates, that can provide heretofore unrecognized benefits.

SUMMARY OF THE INVENTION

The present invention provides combinations of active compounds that can work synergistically to provide improved treatment of various conditions, particularly when administered according to defined dosing regimens. Thus, in one aspect, the invention can provide methods for treating a subject suffering from a defined condition. In particular, the inventive methods can be used to treat a subject suffering from an inflammation related condition. More particularly, the inflammation related condition may be an arthritis related condition, particularly rheumatoid arthritis.

In certain embodiments, a method according to the invention for treating a subject suffering from an inflammation related condition can comprise administering to the subject a first compound according to a first dosing schedule and a second compound according to a second, different dosing schedule. For example, the first compound can be methotrexate or a derivative thereof, and the second compound can be an antifolate compound according to Formula (6):

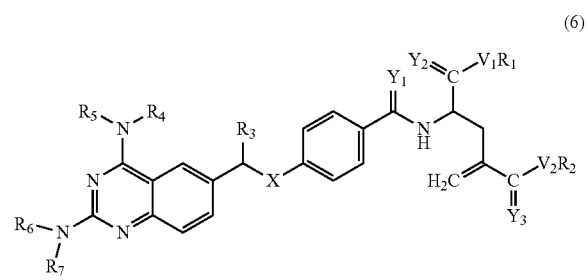

(6)

wherein:
X is $CHR_8$ or $NR_8$;
$Y_1$, $Y_2$, and $Y_3$ independently are O or S;
$V_1$ and $V_2$ independently are O, S, or NZ;
Z is H, optionally substituted alkyl, optionally substituted alkenyl, optionally substituted alkynyl, or alkaryl;
$R_1$ and $R_2$ independently are H, optionally substituted alkyl, optionally substituted alkenyl, optionally substituted alkynyl, or alkaryl;
$R_3$ is H, optionally substituted alkyl, optionally substituted alkenyl, optionally substituted alkynyl, optionally substituted alkoxy, hydroxyl, or halo; and $R_4$, $R_5$, $R_6$, $R_7$, and $R_8$ independently are H, optionally substituted alkyl, optionally substituted alkenyl, optionally substituted alkynyl, acyl, —C(O)-alkyl, —C(O)-alkenyl, or —C(O)-alkynyl; or a pharmaceutically acceptable ester, amide, salt, solvate, enantiomer, or prodrug thereof.

In specific embodiments, the dosing schedules may be similar in scope—e.g., varying only by the time of day at which the compounds are administered. In other embodiments, the dosing schedules may have a greater variance. For example, the dosing schedule for dosing the methotrexate can comprise administering the methotrexate on a weekly basis—e.g., once per week, twice per week, three times per week, or the like. As another example, the dosing schedule for the compound of Formula (6) can comprise administering the compound on a daily schedule—e.g., at least once per day, at least twice per day, or the like. In some embodiments, the compound of Formula (6), for example, could be administered on an intermittent schedule—e.g., administered for one day, two days, three days, etc. followed by one or more days where the compound is not administered. In specific embodiments, the first compound (i.e., methotrexate) and the second compound (i.e., the compound of Formula (6) through Formula (12)) are administered in amounts sufficient to provide a synergistic effect. In other words, the combination acts synergistically to provide a treatment effect that is not attributable merely to a combinatorial effect.

While the second active compound may be characterized as being according to the structure of Formula (6), it is understood that the invention encompasses the group of compounds generally described by said structure, as well as subgroups of the structure that may be defined by further formulas disclosed herein. Thus, the invention can be described as encompassing at least one compound according to any of Formula (6) through Formula (12). Such would apply to not only the methods of the invention but also to various articles of manufacture provided by the invention.

In particular embodiments, the inventive method specifically can encompass combinations comprising at least one compound according to any of Formula (6) through Formula (12) that is in the form of a salt or a di-salt. Specifically, the invention encompasses alkali metal salts of the compounds, more specifically sodium salts, di-sodium salts, potassium salts, and di-potassium salts. In even further embodiments, the invention encompasses combinations comprising at least one compound according to any of Formula (6) through Formula (12) that is a crystalline salt. In other embodiments, the invention specifically encompasses combinations comprising at least one compound according to any of Formula (6) through Formula (12) that is a racemic mixture of two enantiomers or that is enantiomerically purified for a specific enantiomer. For example, the compound according to any of Formula (6) through Formula (12) may exhibit an enantiomeric purity for the (S) enantiomer of at least about 90%. In a specific embodiment, the invention can encompass administering combinations including an antifolate compound according to Formula (12) that is a crystalline, disodium salt in the (S) enantiomeric form exhibiting an enantiomeric purity for the (S) enantiomer of at least about 99%. In another specific embodiment, the invention can encompass administering combinations including an antifolate compound according to Formula (12) that is a crystalline, dipotassium salt in the (S) enantiomeric form exhibiting an enantiomeric purity for the (S) enantiomer of at least about 99%.

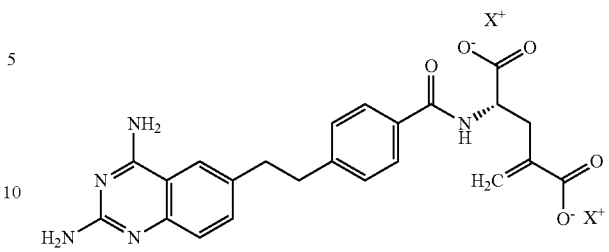

(12)

In another aspect, the present invention also can provide articles of manufacture that are useful for providing a defined dosing regimen of a combination of active compounds as described herein. The articles of manufacture can be particularly beneficial for facilitating proper dosing by a subject since the active compounds can be administered on significantly different schedules or regimens. The articles of manufacture thus can provide the compounds in expressly defined amounts or numbers of doses for administration over a defined period of time such that a subject may readily determine when a dose of any compound in the combination is due for administration and thus may also readily identify whether any prescribed doses have been missed. In certain embodiments, the article of manufacture specifically may be described as a kit that provides the defined dosing regimen, preferably including appropriate instructions for proper dosing of the compounds.

In one embodiment, a kit according to the invention can provide a defined dosing regimen of at least a first active compound and a second active compound, wherein the kit includes a sufficient number of doses of each of the first and second active compounds such that the compositions are dosed in a defined regimen. For example, the defined regimen may specify administration of the active compounds in a defined ratio, such as at least two doses of the second active compound for each one dose of the first active compound. In specific embodiments, the first active compound can be methotrexate or a derivative thereof, and the second active compound may be an antifolate compound according to Formula (6):

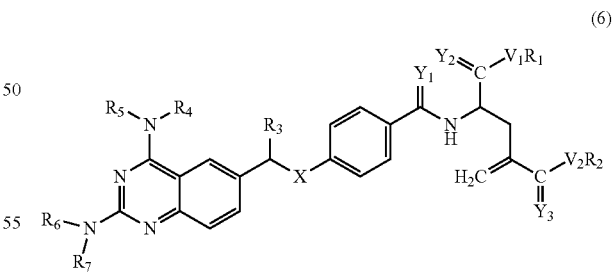

(6)

wherein:
X is $CHR_8$ or $NR_8$;
$Y_1$, $Y_2$, and $Y_3$ independently are O or S;
$V_1$ and $V_2$ independently are O, S, or NZ;
Z is H, optionally substituted alkyl, optionally substituted alkenyl, optionally substituted alkynyl, or alkaryl;
$R_1$ and $R_2$ independently are H, optionally substituted alkyl, optionally substituted alkenyl, optionally substituted alkynyl, or alkaryl;

$R_3$ is H, optionally substituted alkyl, optionally substituted alkenyl, optionally substituted alkynyl, optionally substituted alkoxy, hydroxyl, or halo; and $R_4$, $R_5$, $R_6$, $R_7$, and $R_8$ independently are H, optionally substituted alkyl, optionally substituted alkenyl, optionally substituted alkynyl, acyl, —C(O)-alkyl, —C(O)-alkenyl, or —C(O)-alkynyl; or a pharmaceutically acceptable ester, amide, salt, solvate, enantiomer, or prodrug thereof.

In certain embodiments, the active compounds in the kit may particularly be described as being in the form of pharmaceutical composition. As more fully described herein, such pharmaceutical compositions can comprise a pharmaceutically acceptable carrier and the active compound. Thus, the kit may be described as including a sufficient number of doses of each of the first and second pharmaceutical compositions such that the compositions are dosed in the defined regimen.

The defined dosing regimen may particularly be described in relation to methotrexate being the first active compound in the first pharmaceutical composition, and the antifolate compound according to Formula (6) being the second active compound in the second pharmaceutical composition. For example, in specific embodiments, the kit can include a sufficient number of doses of each of the first and second pharmaceutical compositions such that the compositions are dosed in a regimen of at least one dose per day of the second pharmaceutical composition for each one dose per week of the first pharmaceutical composition. In further embodiments, the kit can include a sufficient number of doses of each of the first and second pharmaceutical compositions such that the compositions are dosed in a regimen of about 7 to about 28 doses per week of the second pharmaceutical composition and 1 to 4 doses per week of the first pharmaceutical composition.

In certain embodiments, a kit (or other article of manufacture) according to the invention can include further components in addition to the active compounds (e.g., pharmaceutical formulations including the active compounds). For example, a kit according to the invention may comprise indicia of the defined dosing regimen instructing proper dosing of the first pharmaceutical composition and the second pharmaceutical composition.

In specific embodiments, the dosing regimen is provided to achieve a desired effect. For example, the dosing regimen can be such that the methotrexate and the antifolate compound according to Formula (6) are provided in dosing amounts sufficient to provide a synergistic effect.

In another aspect, the invention can be described as providing methods of potentiating the effectiveness of methotrexate in the treatment of specific conditions. As further described herein, it has been found that even in treatment of conditions where methotrexate alone may show therapeutic benefit, the effectiveness of treatment may be increased—i.e., potentiated—by combination with one or more of the antifolate compounds described herein in relation to Formula (6) through Formula (12). It is believed that the additional antifolate compound, possibly arising from a more specific mode of action than methotrexate, can act synergistically with the methotrexate to provide a level of therapeutic effect that is not possible with methotrexate alone and that would not have been expected prior to the present invention.

In certain embodiments, the invention specifically provides a method of potentiating the effectiveness of methotrexate in the treatment of rheumatoid arthritis. For example, the method can comprise administering methotrexate or a derivative thereof to a patient suffering from rheumatoid arthritis in combination with an antifolate compound according to Formula (6):

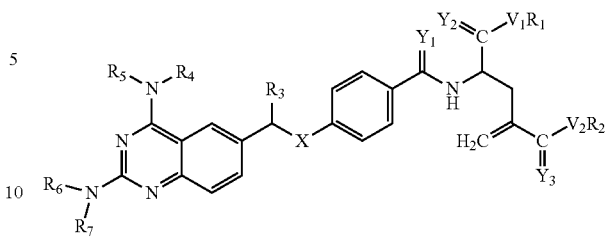

(6)

wherein:
 X is $CHR_8$ or $NR_8$;
 $Y_1$, $Y_2$, and $Y_3$ independently are O or S;
 $V_1$ and $V_2$ independently are O, S, or NZ;
 Z is H, optionally substituted alkyl, optionally substituted alkenyl, optionally substituted alkynyl, or alkaryl;
 $R_1$ and $R_2$ independently are H, optionally substituted alkyl, optionally substituted alkenyl, optionally substituted alkynyl, or alkaryl;
 $R_3$ is H, optionally substituted alkyl, optionally substituted alkenyl, optionally substituted alkynyl, optionally substituted alkoxy, hydroxyl, or halo; and
 $R_4$, $R_5$, $R_6$, $R_7$, and $R_8$ independently are H, optionally substituted alkyl, optionally substituted alkenyl, optionally substituted alkynyl, acyl, —C(O)-alkyl, —C(O)-alkenyl, or —C(O)-alkynyl; or a pharmaceutically acceptable ester, amide, salt, solvate, enantiomer, or prodrug thereof. Preferably, such combination of compounds provides a synergistic effect in the desired treatment.

BRIEF DESCRIPTION OF THE FIGURES

Figure 1:
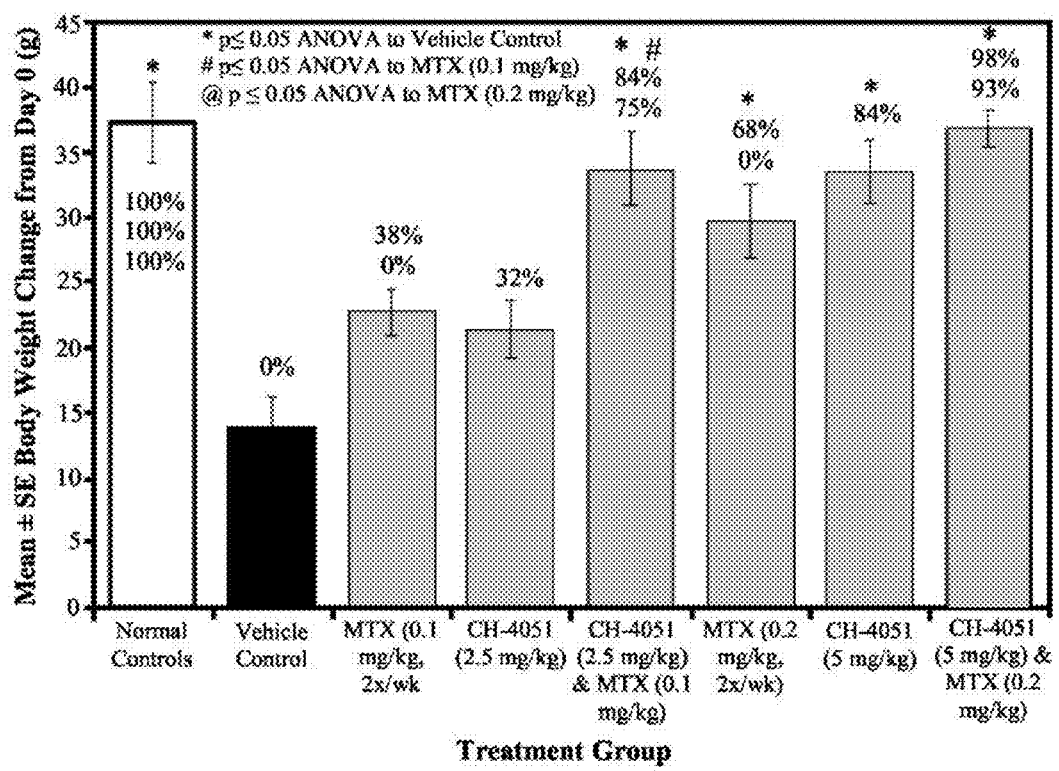
Figure 2:
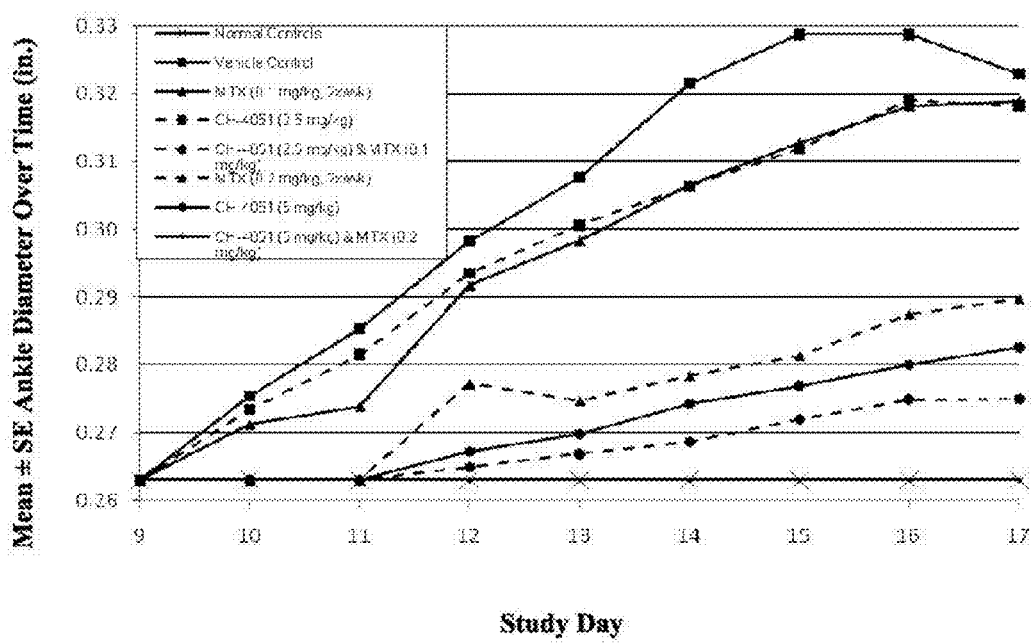
Figure 3:
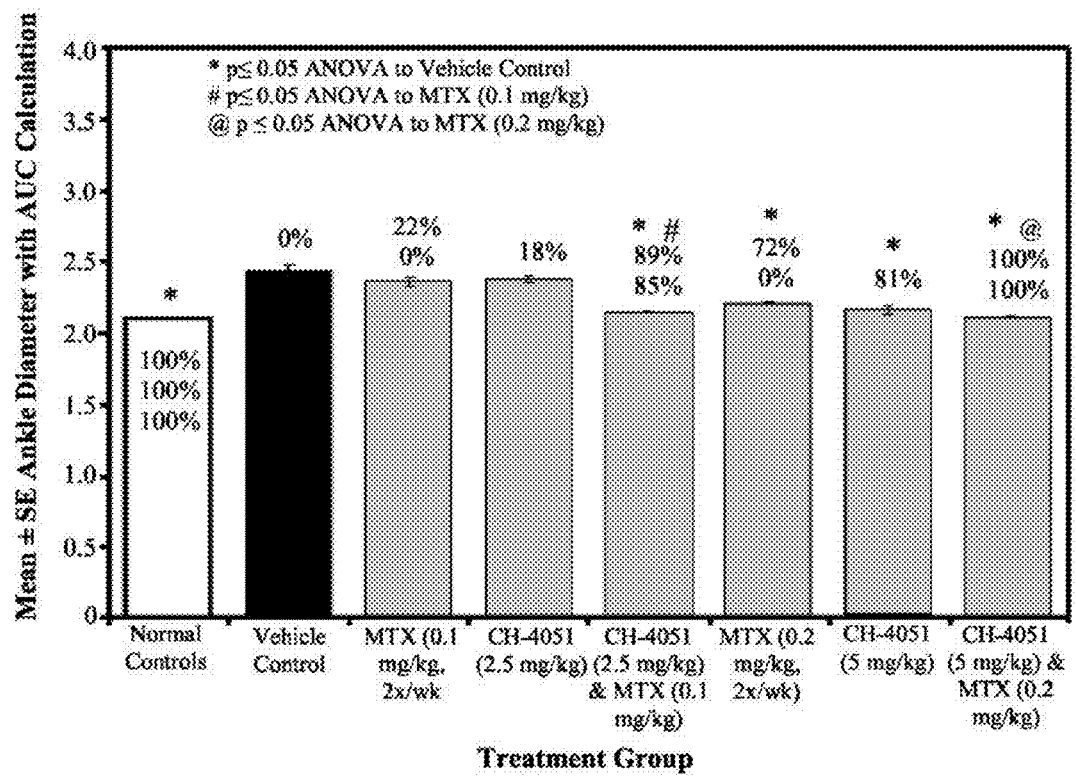
Figure 4:
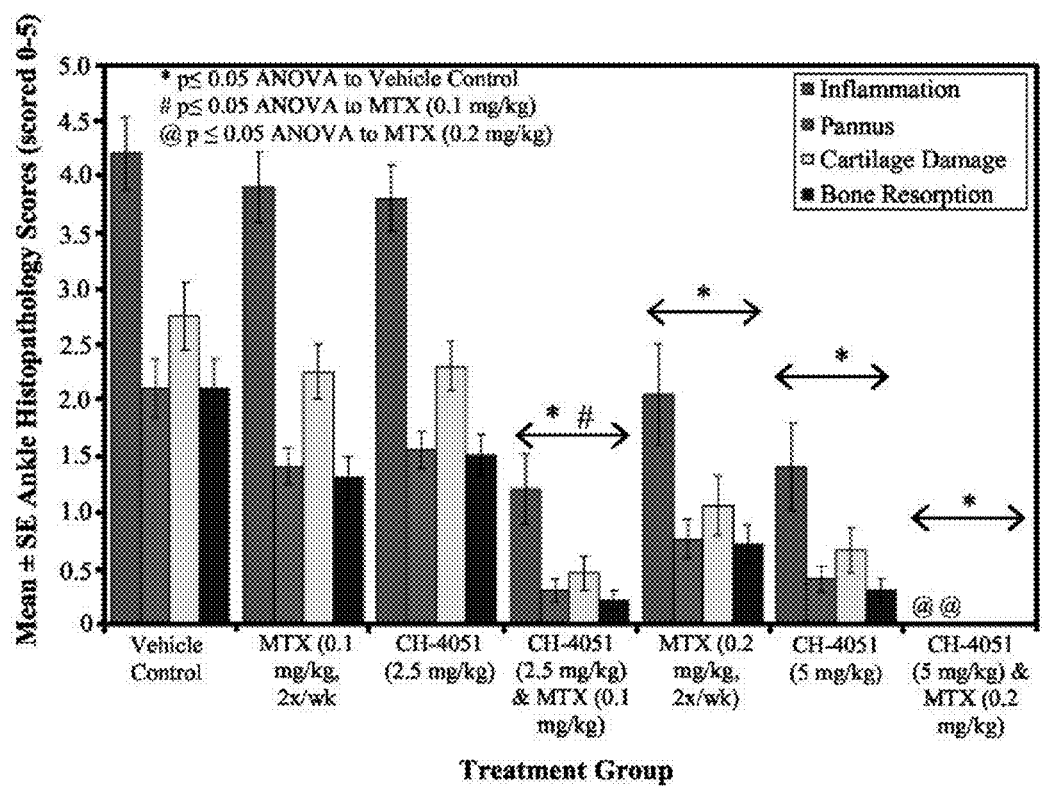
Figure 5:
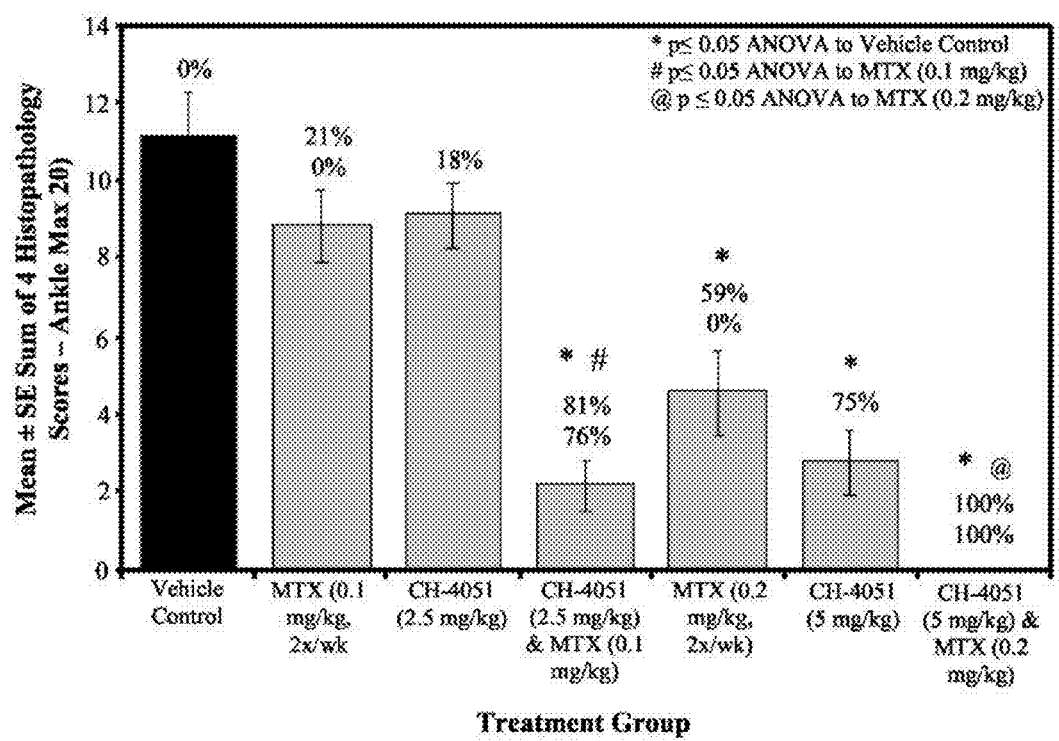
Figure 6:
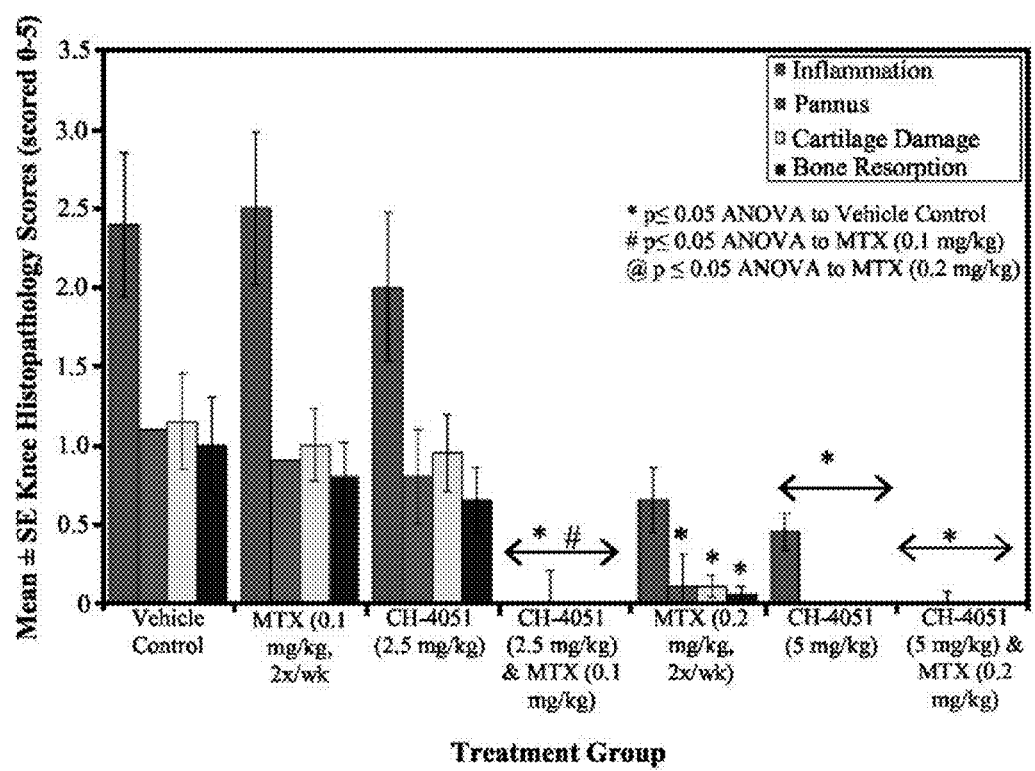
Figure 7:
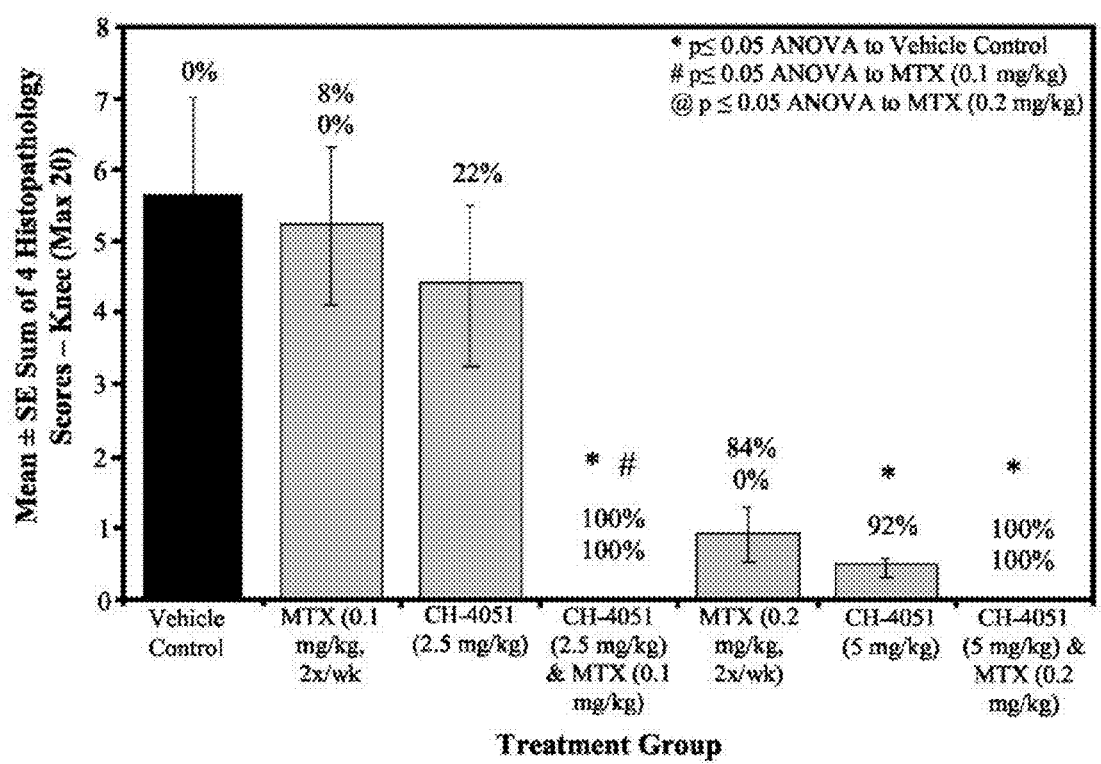
Figure 8:
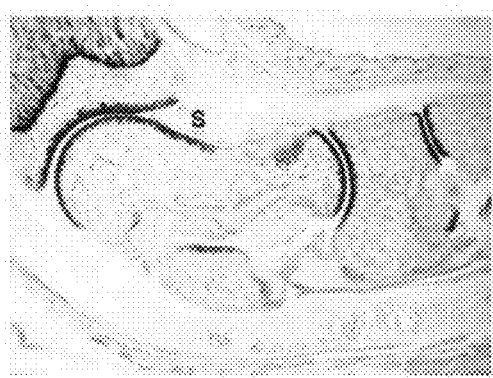
Figure 9:
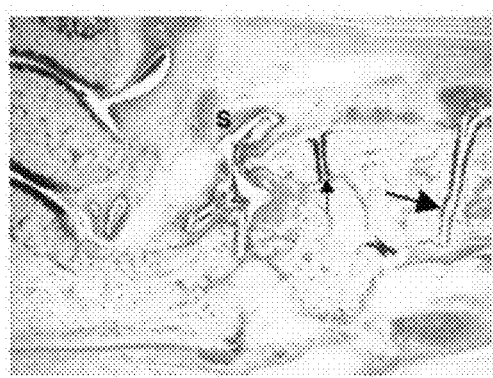
Figure 10:
Figure 11:
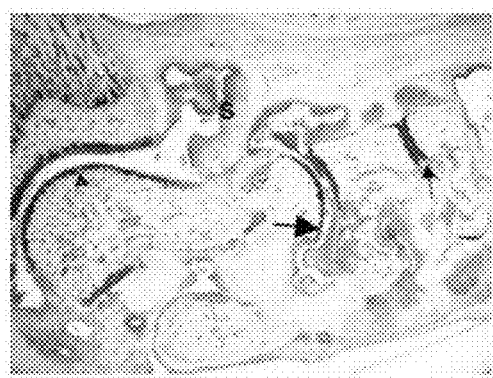
Figure 12:
Figure 13:
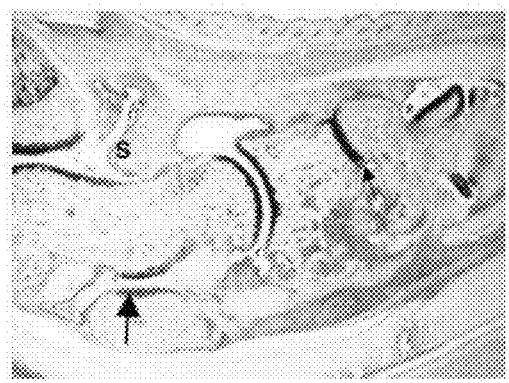
Figure 14:
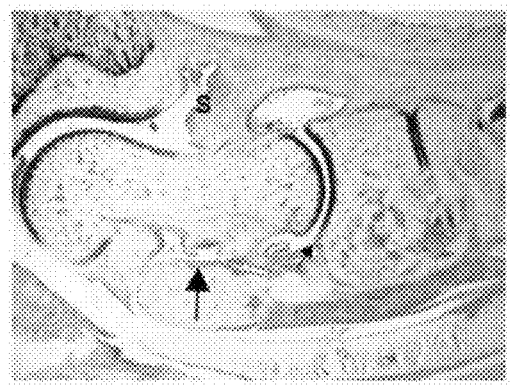
Figure 15:
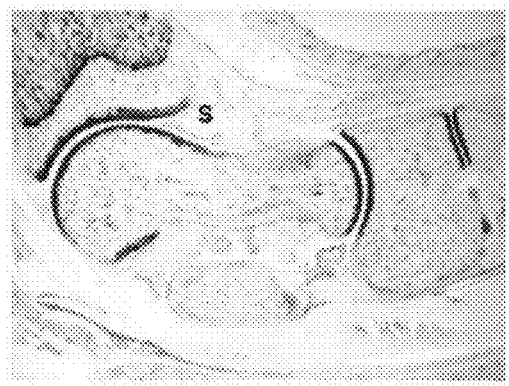
Figure 16:
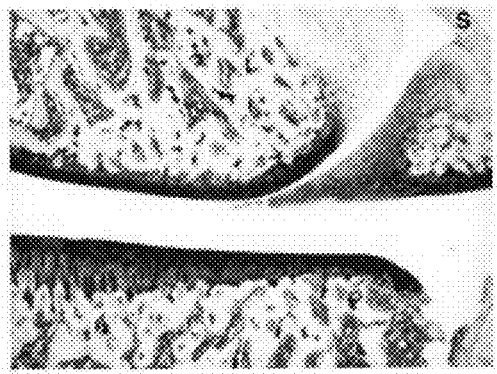
Figure 17:
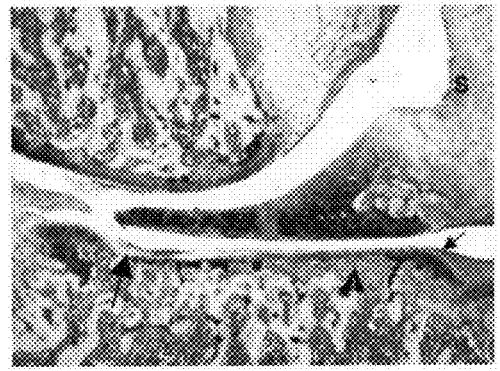
Figure 18:
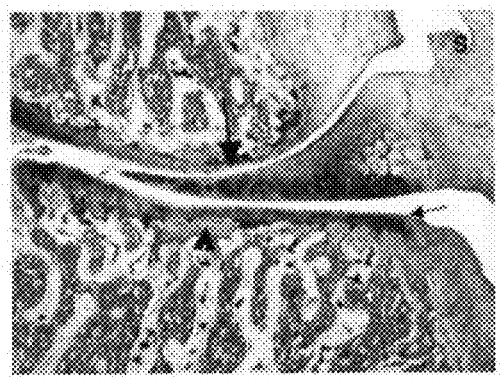
Figure 19:
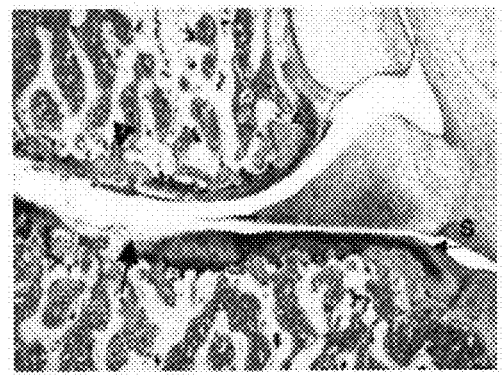
Figure 20:
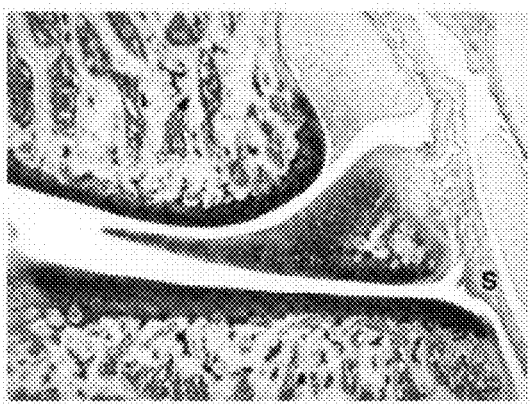
Figure 21:
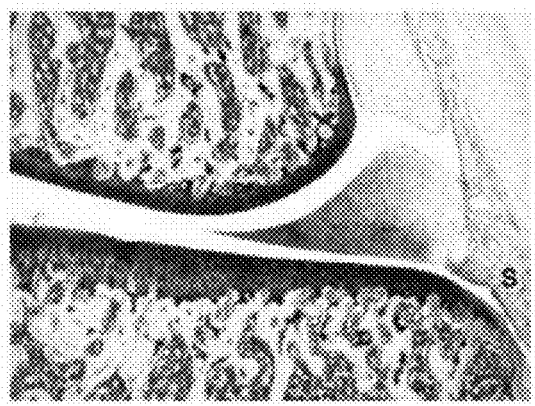
Figure 22:
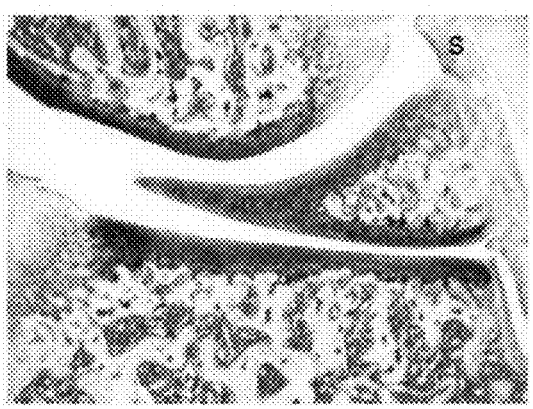
Figure 23:

Having thus described the invention in general terms, reference will now be made to the accompanying figures, which are not necessarily drawn to scale, and wherein:

FIG. 1 is a chart illustrating the effects of treatment on subject body weight according to specific embodiments of the invention in a 17 day rat developing type II collagen arthritis test using the compound CH-4051 alone, methotrexate alone, or CH-4051 and methotrexate in combination;

FIG. 2 is a chart illustrating the effects of treatment on subject ankle diameter according to specific embodiments of the invention in a 17 day rat developing type II collagen arthritis test using the compound CH-4051 alone, methotrexate alone, or CH-4051 and methotrexate in combination;

FIG. 3 is a chart illustrating the effects of treatment on subject ankle diameter with AUC calculation according to specific embodiments of the invention in a 17 day rat developing type II collagen arthritis test using the compound CH-4051 alone, methotrexate alone, or CH-4051 and methotrexate in combination;

FIG. 4 is a chart illustrating the effects of treatment on subject ankle histopathology scores according to specific embodiments of the invention in a 17 day rat developing type II collagen arthritis test using the compound CH-4051 alone, methotrexate alone, or CH-4051 and methotrexate in combination;

FIG. 5 is a chart illustrating the effects of treatment on subject ankle histopathology scores (the sum of four individual scores) according to specific embodiments of the invention in a 17 day rat developing type II collagen arthritis test using the compound CH-4051 alone, methotrexate alone, or CH-4051 and methotrexate in combination;

FIG. 6 is a chart illustrating the effects of treatment on subject knee histopathology scores according to specific embodiments of the invention in a 17 day rat developing type II collagen arthritis test using the compound CH-4051 alone, methotrexate alone, or CH-4051 and methotrexate in combination;

FIG. 7 is a chart illustrating the effects of treatment on subject knee histopathology scores (the sum of four individual scores) according to specific embodiments of the invention in a 17 day rat developing type II collagen arthritis test using the compound CH-4051 alone, methotrexate alone, or CH-4051 and methotrexate in combination;

FIG. 8 is a photomicrograph at 16× magnification showing an image of a normal ankle from an animal in the normal control group (Group 1), wherein the symbol "S" identifies normal synovium;

FIG. 9 is a photomicrograph at 16× magnification showing an image of an ankle from a vehicle control animal (Group 2) evaluated to be illustrative of the approximate mean summed score for all animals in the group, wherein the ankle shows severe inflammation (identified by the symbol "S"), moderate cartilage damage (identified by the large arrow), mild pannus (identified by the small arrow), and bone resorption;

FIG. 10 is a photomicrograph at 16× magnification showing an image of an ankle from an arthritic animal treated with 0.1 mg/kg methotrexate alone (Group 3) evaluated to be illustrative of the approximate mean summed score for all animals in the group, wherein the ankle shows marked inflammation (identified by the symbol "S"), mild cartilage damage (identified by the large arrow), minimal pannus (identified by the small arrow), and bone resorption (identified by the arrow head);

FIG. 11 is a photomicrograph at 16× magnification showing an image of an ankle from an arthritic animal treated with 2.5 mg/kg CH-4051 alone (Group 4) evaluated to be illustrative of the approximate mean summed score for all animals in the group, wherein the ankle shows marked inflammation (identified by the symbol "S"), mild cartilage damage (identified by the large arrow), mild pannus (identified by the small arrow), and bone resorption (identified by the arrow head);

FIG. 12 is a photomicrograph at 16× magnification showing an image of an ankle from an arthritic animal treated with 2.5 mg/kg CH-4051 in combination with 0.1 mg/kg methotrexate (Group 5) evaluated to be illustrative of the approximate mean summed score for all animals in the group, wherein the ankle shows only mild inflammation (identified by the symbol "S");

FIG. 13 is a photomicrograph at 16× magnification showing an image of an ankle from an arthritic animal treated with 0.2 mg/kg methotrexate alone (Group 6) evaluated to be illustrative of the approximate mean summed score for all animals in the group, wherein the ankle shows mild inflammation (identified by the symbol "S"), minimal cartilage damage (identified by the large arrow), minimal pannus (identified by the small arrow), and bone resorption;

FIG. 14 is a photomicrograph at 16× magnification showing an image of an ankle from an arthritic animal treated with 5 mg/kg CH-4051 alone (Group 7) evaluated to be illustrative of the approximate mean summed score for all animals in the group, wherein the ankle shows mild inflammation (identified by the symbol "S"), minimal cartilage damage (identified by the large arrow), and minimal pannus (identified by the small arrow);

FIG. 15 is a photomicrograph at 16× magnification showing an image of an ankle from an arthritic animal treated with 5 mg/kg CH-4051 in combination with 0.2 mg/kg methotrexate (Group 8) evaluated to be illustrative of the approximate mean summed score for all animals in the group, wherein the ankle is normal (the symbol "S" identifying normal synovium);

FIG. 16 is a photomicrograph at 50× magnification showing an image of a normal knee from an animal in the normal control group (Group 1), wherein the symbol "S" identifies normal synovium;

FIG. 17 is a photomicrograph at 50× magnification showing an image of a knee from a vehicle control animal (Group 2) evaluated to have the highest summed score for all animals in the group, wherein the knee shows severe inflammation (identified by the symbol "S"), moderate cartilage damage (identified by the large arrow), moderate pannus (identified by the small arrow), and bone resorption (identified by the arrow head);

FIG. 18 is a photomicrograph at 50× magnification showing an image of a knee from an arthritic animal treated with 0.1 mg/kg methotrexate alone (Group 3) evaluated to have the highest summed score for all animals in the group, wherein the knee shows severe inflammation (identified by the symbol "S"), mild cartilage damage (identified by the large arrow), mild pannus (identified by the small arrow), and bone resorption (identified by the arrow head);

FIG. 19 is a photomicrograph at 50× magnification showing an image of a knee from an arthritic animal treated with 2.5 mg/kg CH-4051 alone (Group 4) evaluated to have the highest summed score for all animals in the group, wherein the knee shows severe inflammation (identified by the symbol "S"), moderate cartilage damage (identified by the large arrow), mild pannus (identified by the small arrow), and bone resorption (identified by the arrow head);

FIG. 20 is a photomicrograph at 50× magnification showing an image of a knee from an arthritic animal treated with 2.5 mg/kg CH-4051 in combination with 0.1 mg/kg methotrexate (Group 5) evaluated to have the highest summed score for all animals in the group, wherein the knee is normal (the symbol "S" identifying normal synovium);

FIG. 21 is a photomicrograph at 50× magnification showing an image of a knee from an arthritic animal treated with 0.2 mg/kg methotrexate alone (Group 6) evaluated to have the highest summed score for all animals in the group, wherein the knee shows mild inflammation (identified by the symbol "S");

FIG. 22 is a photomicrograph at 50× magnification showing an image of a knee from an arthritic animal treated with 5 mg/kg CH-4051 alone (Group 7) evaluated to have the highest summed score for all animals in the group, wherein the knee shows mild inflammation (identified by the symbol "S"); and FIG. 23 is a photomicrograph at 50× magnification showing an image of a knee from an arthritic animal treated with 5 mg/kg CH-4051 in combination with 0.2 mg/kg methotrexate (Group 8) evaluated to have the highest summed score for all animals in the group, wherein the knee is normal (the symbol "S" identifying normal synovium).

DETAILED DESCRIPTION

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The invention provides pharmaceutical compositions comprising antifolate compounds. These compounds can be used in the pharmaceutical composition either directly or in the form of their pharmaceutically active esters, amides, salts, solvates, or prodrugs. In preferred embodiments, the antifolate compounds are in the form of salts, particularly alkali metal salts. The pharmaceutical compositions provide increased activity and bioavailability, even at reduced dosing of the active antifolate compounds, and the pharmaceutical compositions are useful in the treatment of a number of conditions and diseases, particularly for the treatment of abnormal cell proliferation, inflammation, arthritis, or asthma.

The term "metabolically inert antifolate" as used herein means compounds that are (i) folic acid analogs capable of disrupting folate metabolism and (ii) non-polyglutamylatable. In certain embodiments, the term can mean compounds that are also (iii) non-hydroxylatable.

The term "alkali metal" as used herein means Group IA elements and particularly includes sodium, lithium, and potassium; the term "alkali metal salt" as used herein means an ionic compound wherein the cation moiety of the compound comprises an alkali metal, particularly sodium, lithium, or potassium.

The term "alkyl" as used herein means saturated straight, branched, or cyclic hydrocarbon groups. In particular embodiments, alkyl refers to groups comprising 1 to 10 carbon atoms ("$C_{1-10}$ alkyl"). In further embodiments, alkyl refers to groups comprising 1 to 8 carbon atoms ("$C_{1-8}$ alkyl"), 1 to 6 carbon atoms ("$C_{1-6}$ alkyl"), or 1 to 4 carbon atoms ("$C_{1-4}$ alkyl"). In specific embodiments, alkyl refers to methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. Substituted alkyl refers to alkyl substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$; hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate.

The term "alkenyl" as used herein means alkyl moieties wherein at least one saturated C—C bond is replaced by a double bond. In particular embodiments, alkenyl refers to groups comprising 1 to 10 carbon atoms ("$C_{1-10}$ alkenyl"). In further embodiments, alkenyl refers to groups comprising 1 to 8 carbon atoms ("$C_{1-8}$ alkenyl"), 1 to 6 carbon atoms ("$C_{1-6}$ alkenyl"), or 1 to 4 carbon atoms ("$C_{1-4}$ alkenyl"). In specific embodiments, alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl. Substituted alkenyl refers to alkenyl substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$; hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate.

The term "alkynyl" as used herein means alkynyl moieties wherein at least one saturated C—C bond is replaced by a triple bond. In particular embodiments, alkynyl refers to groups comprising 1 to 10 carbon atoms ("$C_{1-10}$ alkynyl"). In further embodiments, alkynyl refers to groups comprising 1 to 8 carbon atoms ("$C_{1-8}$ alkynyl"), 1 to 6 carbon atoms ("$C_{1-6}$ alkynyl"), or 1 to 4 carbon atoms ("$C_{1-4}$ alkynyl"). In specific embodiments, alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl. Substituted alkynyl refers to alkynyl substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$; hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate.

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 10 carbon atoms ("$C_{1-10}$ alkoxy"). In further embodiments, alkoxy refers to oxygen-linked groups comprising 1 to 8 carbon atoms ("$C_{1-8}$ alkoxy"), 1 to 6 carbon atoms ("$C_{1-6}$ alkoxy"), or 1 to 4 carbon atoms ("$C_{1-4}$ alkoxy"). Substituted alkoxy refers to alkoxy substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$; hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate.

The term "halo" or "halogen" as used herein means fluorine, chlorine, bromine, or iodine.

The term "aryl" as used herein means a stable monocyclic, bicyclic, or tricyclic carbon ring of up to 8 members in each ring, wherein at least one ring is aromatic as defined by the Hückel 4n+2 rule. Exemplary aryl groups according to the invention include phenyl, naphthyl, tetrahydronaphthyl, and biphenyl. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate.

The terms "aralkyl" and "arylalkyl" as used herein mean an aryl group as defined above linked to the molecule through an alkyl group as defined above.

The terms "alkaryl" and "alkylaryl" as used herein means an alkyl group as defined above linked to the molecule through an aryl group as defined above.

The term "acyl" as used herein means a carboxylic acid ester in which the non-carbonyl moiety of the ester group is selected from straight, branched, or cyclic alkyl or lower alkyl; alkoxyalkyl including methoxymethyl; aralkyl including benzyl; aryloxyalkyl such as phenoxymethyl; aryl including phenyl optionally substituted with halogen, $C_1$-$C_6$ alkyl or $C_1$-$C_6$ alkoxy; sulfonate esters such as alkyl or aralkyl sulphonyl including methanesulfonyl; mono-phosphate ester, di-phosphate ester, or tri-phosphate ester; trityl or monomethoxytrityl; substituted benzyl; trialkylsilyl such as dimethyl-t-butylsilyl or diphenylmethylsilyl. Aryl groups in the esters preferably comprise a phenyl group.

The term "amino" as used herein means a moiety represented by the structure $NR_2$, and includes primary amines, and secondary and tertiary amines substituted by alkyl (i.e., alkylamino). Thus, $R_2$ may represent two hydrogen atoms, two alkyl moieties, or one hydrogen atom and one alkyl moiety.

The terms "alkylamino" and "arylamino" as used herein mean an amino group that has one or two alkyl or aryl substituents, respectively.

The term "analogue" as used herein means a compound in which one or more individual atoms or functional groups have been replaced, either with a different atom or a different functional, generally giving rise to a compound with similar properties.

The term "derivative" as used herein means a compound that is formed from a similar, beginning compound by attaching another molecule or atom to the beginning compound. Further, derivatives, according to the invention, encompass one or more compounds formed from a precursor compound through addition of one or more atoms or molecules or through combining two or more precursor compounds.

The term "prodrug" as used herein means any compound which, when administered to a mammal, is converted in whole or in part to a compound of the invention.

The term "active metabolite" as used herein means a physiologically active compound which results from the metabolism of a compound of the invention, or a prodrug thereof, when such compound or prodrug is administered to a mammal.

The terms "therapeutically effective amount" or "therapeutically effective dose" as used herein are interchangeable and mean a concentration of a compound according to the invention, or a biologically active variant thereof, sufficient to elicit the desired therapeutic effect according to the methods of treatment described herein.

The term "pharmaceutically acceptable carrier" as used herein means a carrier that is recognized as useful in the art to facilitate the storage, administration, and/or the healing effect of a biologically active agent.

The term "intermittent administration" as used herein means administration of a therapeutically effective dose of a composition according to the invention, followed by a time period of discontinuance, which is then followed by another administration of a therapeutically effective dose, and so forth.

The term "potentiate" as used herein means to increase the effectiveness of an agent in relation to a particular desired end result. The term specifically can be used to describe a synergistic effect achieved by the combination of two or more active agents wherein the combination of the active agents provides an effectiveness that exceeds the effectiveness of any of the agents alone in relation to a particular desired end result.

The term "antiproliferative agent" as used herein means a compound that decreases the hyperproliferation of cells.

The term "abnormal cell proliferation" as used herein means a disease or condition characterized by the inappropriate growth or multiplication of one or more cell types relative to the growth of that cell type or types in an individual not suffering from that disease or condition.

The term "cancer" as used herein means a disease or condition characterized by uncontrolled, abnormal growth of cells, which can spread locally or through the bloodstream and lymphatic system to other parts of the body. The term includes tumor-forming or non-tumor forming cancers, and includes various types of cancers, such as primary tumors and tumor metastasis.

The term "tumor" as used herein means an abnormal mass of cells within a multicellular organism that results from excessive cell division that is uncontrolled and progressive, also called a neoplasm. A tumor may either be benign or malignant.

The term "fibrotic disorders" as used herein means fibrosis and other medical complications of fibrosis which result in whole or in part from the proliferation of fibroblasts.

The term "arthritis" as used herein means an inflammatory disorder affecting joints that can be infective, autoimmune, or traumatic in origin.

Chemical nomenclature using the symbols "D" and "L" or "R" and "S" are understood to relate the absolute configuration, or three-dimensional arrangement, of atoms or groups around a chiral element, which may be a center, usually an atom, an axis, or a plane. As used herein, the "D/L" system and the "R/S" systems are meant to be used interchangeably such that "D" in the former system corresponds to "R" in the later system and "L" in the former system corresponds to "S" in the later system.

The present invention arises from a specific recognition that combinations of antifolate compounds can surprisingly provide beneficial effects exceeding the effectiveness of the agents when used alone. In particular, it is believed that because of different mechanisms of action of different antifolate compounds, the combination of two or more antifolate compounds acting by two or more different mechanisms can result in a synergistic effect that would not necessarily be expected. Although mechanisms of action of different types of antifolate compounds have been previously described, it has not been previously recognized that combining different antifolate compounds with different mechanisms of action could actually potentiate the effectiveness of one or more of the compounds in its treatment of specific conditions. In some embodiments, the combination can be made such that the active agents are provided in a defined dosing regimen, and such defined dosing regimens are further described herein. In certain embodiments, the combinations are such that the active compounds are provided in separate dosing forms to facilitate the defined dosing regimen. Further description of the administration of the compounds in relation to dosing regimens, dosing forms, dosing amounts, and the like is provided herein.

In specific embodiments, at least one active agent (or active compound) used in the combinations of the invention comprises an antifolate compound having the structure provided in Formula (6),

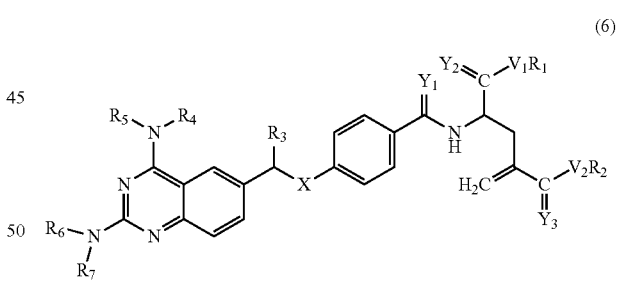

wherein:
X is $CHR_8$ or $NR_8$;
$Y_1$, $Y_2$, and $Y_3$ independently are O or S;
$V_1$ and $V_2$ independently are O, S, or NZ;
Z is H, optionally substituted alkyl, optionally substituted alkenyl, optionally substituted alkynyl, or alkaryl;
$R_1$ and $R_2$ independently are H, optionally substituted alkyl, optionally substituted alkenyl, optionally substituted alkynyl, or alkaryl;
$R_3$ is H, optionally substituted alkyl, optionally substituted alkenyl, optionally substituted alkynyl, optionally substituted alkoxy, hydroxyl, or halo; and
$R_4$, $R_5$, $R_6$, $R_7$, and $R_8$ independently are H, optionally substituted alkyl, optionally substituted alkenyl, optionally substituted alkynyl, acyl, —C(O)-alkyl, —C(O)-alkenyl, or —C(O)-alkynyl; as well as pharmaceutically acceptable esters, amides, salts, solvates, enantiomers, and prodrugs thereof.

In another embodiment, at least one active agent used in the combinations of the invention comprises an antifolate compound having the structure provided in Formula (7)

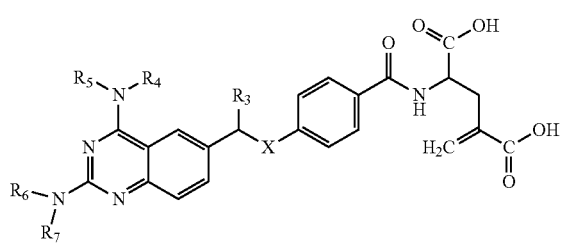

(7)

wherein:

X is $CHR_8$ or $NR_8$;

$R_3$ is H, optionally substituted alkyl, optionally substituted alkenyl, optionally substituted alkynyl, optionally substituted alkoxy, hydroxyl, or halo; and $R_4$, $R_5$, $R_6$, $R_7$, and $R_8$ independently are H, optionally substituted alkyl, optionally substituted alkenyl, optionally substituted alkynyl, acyl, —C(O)-alkyl, —C(O)-alkenyl, or —C(O)-alkynyl; as well as pharmaceutically acceptable esters, amides, salts, solvates, enantiomers, and prodrugs thereof.

In yet another embodiment, at least one active agent used in the combinations of the invention comprises an antifolate compound having the structure provided in Formula (8)

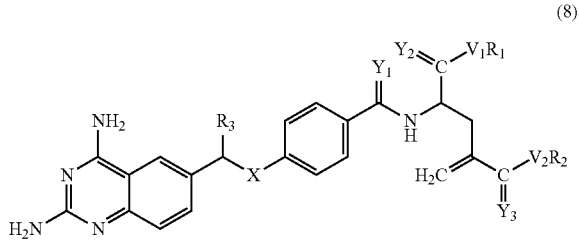

(8)

wherein:

X is $CHR_8$ or $NR_8$;

$Y_1$, $Y_2$, and $Y_3$ independently are O or S;

$V_1$ and $V_2$ independently are O, S, or NZ;

Z is H, optionally substituted alkyl, optionally substituted alkenyl, optionally substituted alkynyl, or alkaryl;

$R_1$ and $R_2$ independently are H, optionally substituted alkyl, optionally substituted alkenyl, optionally substituted alkynyl, or alkaryl;

$R_3$ is H, optionally substituted alkyl, optionally substituted alkenyl, optionally substituted alkynyl, optionally substituted alkoxy, hydroxyl, or halo; and $R_8$ is H, optionally substituted alkyl, optionally substituted alkenyl, optionally substituted alkynyl, acyl, —C(O)-alkyl, —C(O)-alkenyl, or —C(O)-alkynyl as well as pharmaceutically acceptable esters, amides, salts, solvates, enantiomers, and prodrugs thereof.

In particular embodiments, at least one active agent used in the combinations of the invention comprises an antifolate compound having the structure provided in Formula (9).

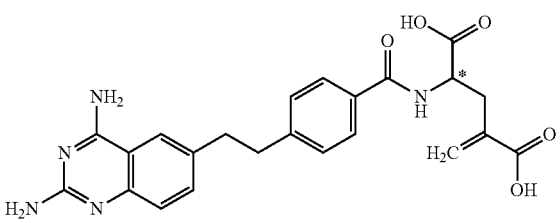

(9)

This compound may particularly be known by the name 2-{4-[2-(2,4-diamino-quinazolin-6-yl)-ethyl]-benzoylamino}-4-methylene-pentanedioic acid. The compound may also be known as gamma methylene glutamate 5,8,10-trideaza aminopterin or 5,8-dideaza MDAM. The antifolate compound of Formula (9) is non-polyglutamylatable, non-hydroxylatable, and capable of disrupting folate metabolism.

Biologically active variants of the various compounds described herein are also encompassed by the invention. Such variants should retain the general biological activity of the original compounds; however, the presence of additional activities would not necessarily limit the use thereof in the present invention. Such activity may be evaluated using standard testing methods and bioassays recognizable by the skilled artisan in the field as generally being useful for identifying such activity.

According to some embodiments of the invention, suitable biologically active variants comprise one or more analogues or derivatives of the compounds described herein. Indeed, a single compound useful according to the invention may give rise to an entire family of analogues or derivatives having similar activity and, therefore, usefulness according to the present invention. Likewise, a single compound useful according to the invention may represent a single family member of a greater class of compounds useful according to the present invention. Accordingly, the present invention fully encompasses not only the compounds described herein, but analogues and derivatives of such compounds, particularly those identifiable by methods commonly known in the art and recognizable to the skilled artisan.

The compounds disclosed herein may contain chiral centers, which may be either of the (R) or (S) configuration, or may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the present compounds.

The compound of Formula (9), for example, is a chiral compound, the chiral center being indicated with an asterisk. Accordingly, the antifolate compound of Formula (9) can exist as two separate enantiomers—either the (R) enantiomer or the (S) enantiomer. Typically, the antifolate compound of Formula (9) exists as a racemic mixture of the two enantiomers.

Various methods are known in the art for preparing optically active forms and determining activity. Such methods include standard tests described herein and other similar tests which are well known in the art. Examples of methods that can be used to obtain optical isomers of the compounds useful according to the present invention include the following:

i) physical separation of crystals whereby macroscopic crystals of the individual enantiomers are manually separated. This technique may particularly be used when crystals of the separate enantiomers exist (i.e., the material is a conglomerate), and the crystals are visually distinct;

ii) simultaneous crystallization whereby the individual enantiomers are separately crystallized from a solution of the racemate, possible only if the latter is a conglomerate in the solid state;

iii) enzymatic resolutions whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis whereby the desired enantiomer is synthesized from an achiral precursor under conditions that produce asymmetry (i.e., chirality) in the product, which may be achieved using chiral catalysts or chiral auxiliaries;

vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors whereby the desired enantiomer is obtained from non-chiral starting materials and where the stereochemical integrity is not or is only minimally compromised over the course of the synthesis;

x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography whereby the racemate is volatilized and enantiomers are separated by virtue of their differing interactions in the gaseous mobile phase with a column containing a fixed non-racemic chiral adsorbent phase;

xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

In one embodiment, an active agent used in the combinations of the invention comprises the antifolate compound (S)-2-{4-[2-(2,4-diamino-quinazolin-6-yl)-ethyl]-benzoylamino}-4-methylene-pentanedioic acid, which is shown in Formula (10). The compound of Formula (10) is the (S) enantiomer of the compound shown in Formula (9). The (S) enantiomer can be particularly useful in the combinations of the invention in light of its increased activity in comparison to the (R) enantiomer.

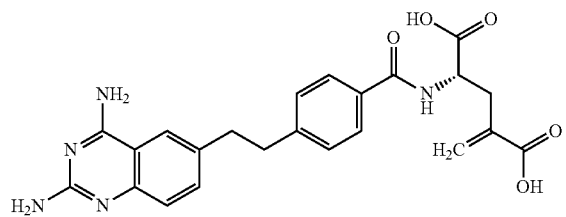

(10)

The antifolate compounds used in the inventive combinations optionally may be provided in an enantiomerically enriched form, such as a mixture of enantiomers in which one enantiomer is present in excess (given as a mole fraction or a weight fraction). Enantiomeric excess is understood to exist where a chemical substance comprises two enantiomers of the same compound and one enantiomer is present in a greater amount than the other enantiomer. Unlike racemic mixtures, these mixtures will show a net optical rotation. With knowledge of the specific rotation of the mixture and the specific rotation of the pure enantiomer, the enantiomeric excess (abbreviated "ee") can be determined by known methods. Direct determination of the quantities of each enantiomer present in the mixture (e.g., as a weight %) is possible with NMR spectroscopy and chiral column chromatography.

For example, in one embodiment, the combinations of the invention can comprise a compound according to Formula (9), wherein the (S) enantiomer, as shown in Formula (10), is present in an enantiomeric excess. Thus, the compound of Formula (9) can be referred to as being in an optically purified form in relation to the (S) enantiomer. Likewise, the combinations comprising an enantiomeric excess of the (S) enantiomer can be referred to as having a specific enantiomeric purity.

The use of the term "entantiomerically pure" or "enantiomeric purity" should not be construed as limiting the combinations of the invention to compounds that are 100% pure for the specific enantiomeric. Rather, the terms are understood as indicating that the racemic mix (i.e., 50/50 mixture of the enantiomers) has been purified such that one enantiomer comprises greater than 50% of the total amount of the compound present. In other words, the antifolate compounds used in the combinations of the invention can be enantiomerically pure for the (S) enantiomer such that greater than 50% of the compound present in the composition is the (S) enantiomer. In specific embodiments, the combinations of the invention can comprise an antifolate compound described herein having an enantiomeric purity for one enantiomer, such as the (S) enantiomer, of at least about 75%. In other words, at least about 75% of the antifolate compound is in the desired enantiomeric form. In further embodiments, the antifolate compounds described herein used in the inventive combinations can have an enantiomeric purity for the desired enantiomer of at least about 80%, at least about 85%, at least about 90%, at least about 95%, at least about 96%, at least about 97%, at least about 98%, at least about 99%, at least about 99.5%, at least about 99.6%, at least about 99.7%, or at least about 99.8%.

The compounds described herein for use in the inventive combinations can, in certain embodiments, be in the form of an ester, amide, salt, solvate, prodrug, or metabolite provided they maintain pharmacological activity according to the present invention. Esters, amides, salts, solvates, prodrugs, and other derivatives of the compounds of the present invention may be prepared according to methods generally known in the art, such as, for example, those methods described by J. March, Advanced Organic Chemistry: Reactions, Mechanisms and Structure, 4$^{th}$ Ed. (New York: Wiley-Interscience, 1992), which is incorporated herein by reference.

Examples of pharmaceutically acceptable salts of the compounds useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates. An acid addition salt may be reconverted to the free base by treatment with a suitable base.

If a compound of the invention is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

If a compound useful according to the invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

Esters of the compounds according to the present invention may be prepared through functionalization of hydroxyl and/or carboxyl groups that may be present within the molecular structure of the compound Amides and prodrugs may also be prepared using techniques known to those skilled in the art. For example, amides may be prepared from esters, using suitable amine reactants, or they may be prepared from anhydride or an acid chloride by reaction with ammonia or a lower alkyl amine. Moreover, esters and amides of compounds of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the invention in combination with water, isopropanol, ethanol, methanol, DMSO, ethyl acetate, acetic acid, or ethanolamine.

In particular embodiments, an antifolate compound used in the inventive combinations can comprise a salt of the antifolate compounds described above. In specific embodiments, the inventive combinations can comprise a salt compound according to Formula (11).

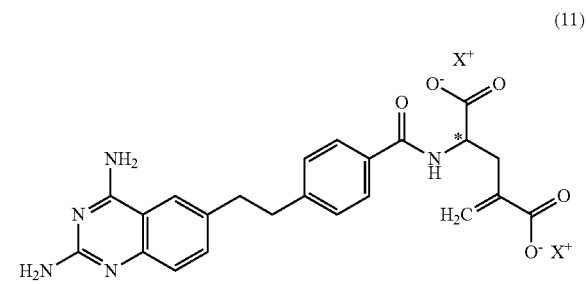

(11)

In Formula (11), the asterisk again denotes a chiral center, X$^+$ can be any suitable salt-forming counterion, and each X$^+$ can be the same or different. In specific embodiments, X$^+$ is an alkali metal. In one preferred embodiment, X$^+$ is a sodium cation. In another preferred embodiment, X$^+$ is a potassium cation. In a specific embodiment, one active agent used in the combinations of the invention comprises a disodium salt according to Formula (11). In still another specific embodiment, one active agent used in the combinations of the invention comprises a dipotassium salt according to Formula (11). Of course, it is understood that other cationic moieties could be used as X$^+$ in the compound of Formula (11). Moreover, the invention also encompasses salt forms according to Formula (11) that can be enantiomerically pure for the (R) enantiomer, enantiomerically pure for the (S) enantiomer, or in a racemic form. Such enantiomeric purity can be as previously described above. For example, in one embodiment, a compound useful in the inventive combinations can be a disodium salt or a dipotassium salt of 2-{4-[2-(2,4-diamino-quinazolin-6-yl)-ethyl]-benzoylamino}-4-methylene-pentanedioic acid that is enantiomerically purified for the (S) enantiomer, as described above. Accordingly, the combinations can comprise a compound according to Formula (12), which is a salt of (S)-2-{4-[2-(2,4-diamino-quinazolin-6-yl)-ethyl]-benzoylamino}-4-methylene-pentanedioic acid, and wherein X+ is as defined above in relation to Formula (11). Preferably, the compound is at least 95% pure for the (S) enantiomer, more preferably at least 97% pure, still more preferably at least 98% pure, even more preferably at least 99% pure, and most preferably at least 99.5% pure for the (S) enantiomer.

(12)

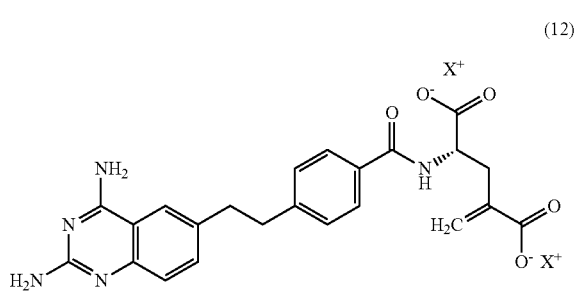

In the case of solid compositions, it is understood that the compounds used in the combinations of the invention may exist in different forms. For example, the compounds may exist in stable and metastable crystalline forms and isotropic and amorphous forms, all of which are intended to be within the scope of the present invention. Crystalline and amorphous forms of the inventive compounds can be characterized by the unique X-ray powder diffraction pattern (i.e., interplanar spacing peaks expressed in Angstroms) of the material. Equipment useful for measuring such data is known in the art, such as a Shimadzu XRD-6000 X-ray diffractometer, and any such equipment can be used to measure the compounds according to the present invention.

In some embodiments, the compounds of Formula (12) may be referenced in relation to the label "CH-4051." This term relates to di-salts of the enantiomerically purified compound, and may specifically relate to the dipotassium salt or the disodium salt. Again, the term CH-4051 may refer to the compounds in one or more the possible forms discussed above.

The active compounds of the present invention may comprise prodrugs and/or active metabolites of the antifolate compounds described herein. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. In preferred embodiments, the compounds of this invention possess anti-proliferative activity against abnormally proliferating cells and/or anti-inflammatory activity, particularly anti-rheumatic activity, or are metabolized to a compound that exhibits one or more of such activities.

A number of prodrug ligands are known. In general, alkylation, acylation, or other lipophilic modification of one or more heteroatoms of the compound, such as a free amine or carboxylic acid residue, reduces polarity and allows passage into cells. Examples of substituent groups that can replace one or more hydrogen atoms on the free amine and/or carboxylic acid moiety include, but are not limited to, the following: aryl; steroids; carbohydrates (including sugars); 1,2-diacylglycerol; alcohols; acyl (including lower acyl); alkyl (including lower alkyl); sulfonate ester (including alkyl or arylalkyl sulfonyl, such as methanesulfonyl and benzyl, wherein the phenyl group is optionally substituted with one or more substituents as provided in the definition of an aryl given herein); optionally substituted arylsulfonyl; lipids (including phospholipids); phosphotidylcholine; phosphocholine; amino acid residues or derivatives; amino acid acyl residues or derivatives; peptides; cholesterols; or other pharmaceutically acceptable leaving groups which, when administered in vivo, provide the free amine and/or carboxylic acid moiety. Any of these can be used in combination with the disclosed compounds to achieve a desired effect.

Various processes for synthesizing antifolate compounds are disclosed in U.S. Pat. No. 4,996,207, U.S. Pat. No. 5,550,128, Abraham et al. (1991) *J. Med. Chem.* 34:222-227, and Rosowsky et al. (1991) *J. Med. Chem.* 34:203-208, all of which are incorporated herein by reference. As one example of a method of synthesis, the compound according to Formula (12) can be prepared according to Reaction Scheme I, shown below.

Reaction Scheme I

Step 1

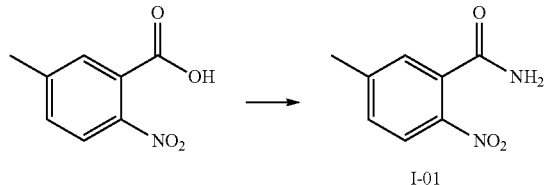

I-01

-continued
Step 2
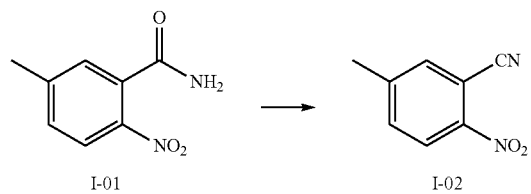
Step 3
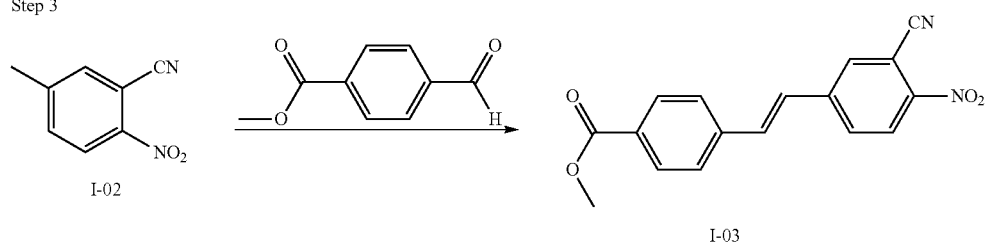
Step 4
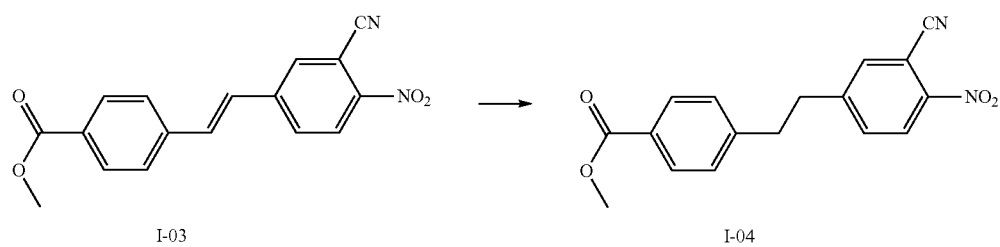
Step 5
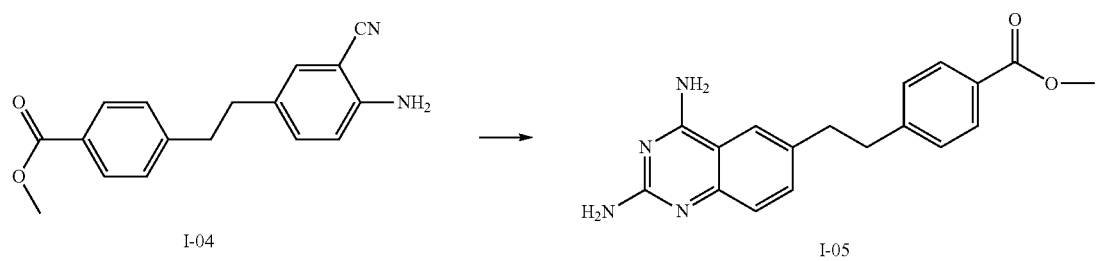
Step 6
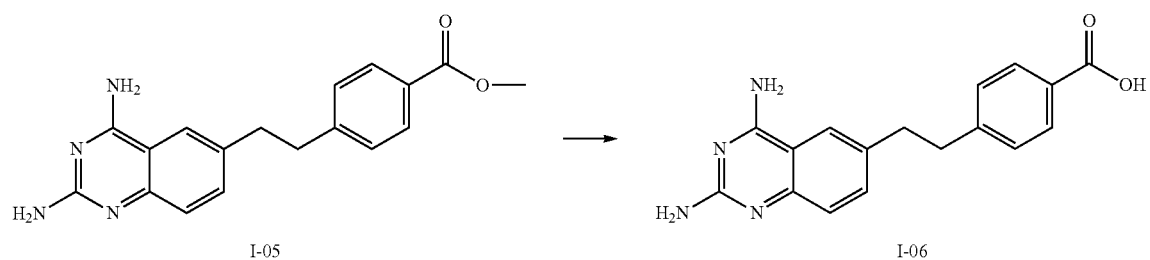
Step 7
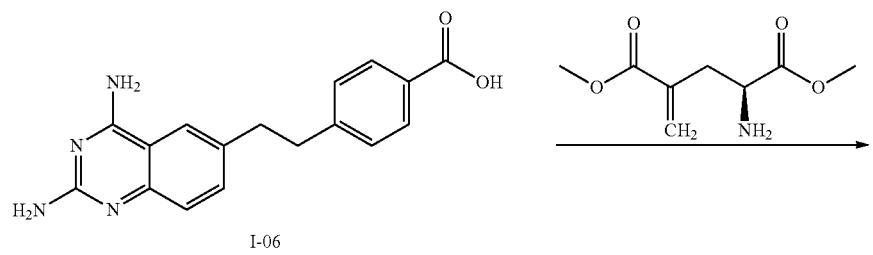

-continued
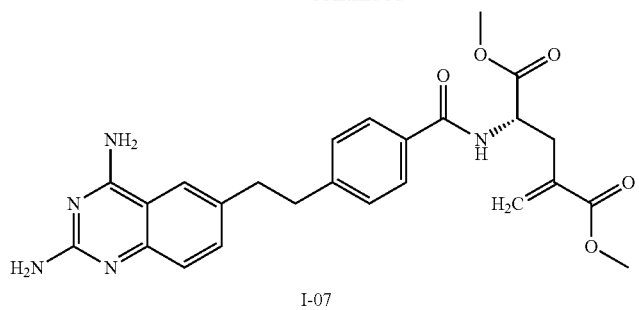
I-07
Step 8
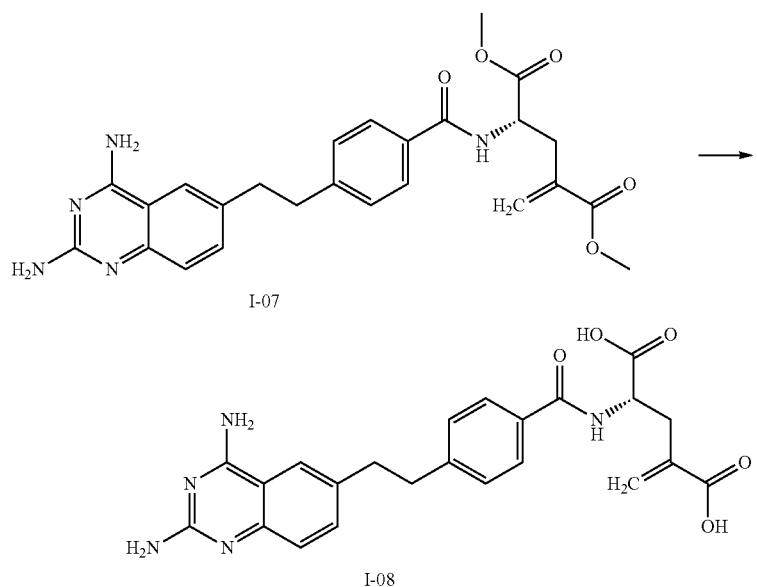
Step 9
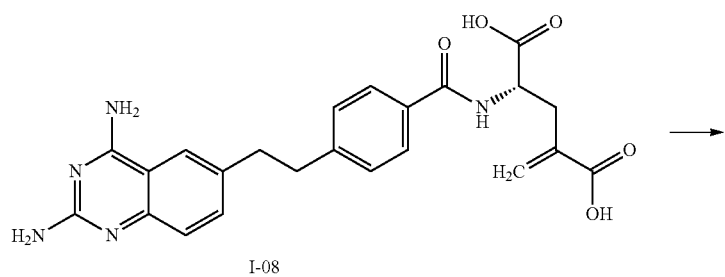
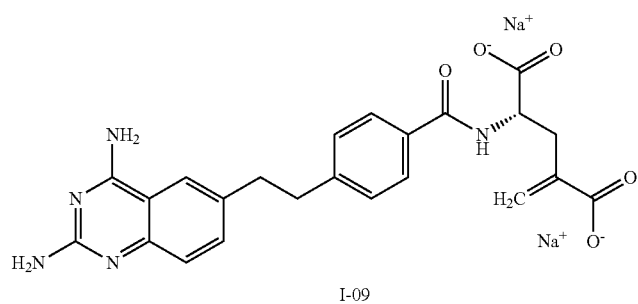
I-09

According to Reaction Scheme 1,6-nitro-m-toluic acid is converted to intermediate compound I-01 via reaction with a carboxylate activator, such as isobutyl chloroformate, and triethylamine. Compound I-01 is then converted to the cyanate form (1-02), such as by reacting with phosphorus oxychloride in dimethylformamide. In step 3, compound I-02 is reacted with 4-methoxycarbonyl-benzaldehyde in a suitable solvent, such as tetrahydrofuran, in the presence of a nucleophilic organocatalyst, such as 1,1,3,3-tetramethylguanidine to form compound I-03. This compound is then hydrogenated in the presence of a suitable catalyst, such as carbon-supported palladium, preferably in a suitable solvent, such as tetrahydrofuran, to form compound I-04. In step 5, the fused ring compound I-05 is formed by reacting compound I-04 (in a solution of sulfolane) with chloroformamidine hydrochloride. Compound I-05 is converted to the carboxylic acid compound I-06 (4-[2-(-2,4-diamino-quinazolin-6-yl)ethyl]benzoic acid), such as by refluxing in a base and organic solvent, evaporating the solvent, and acidifying the remaining material. In step 7, compound I-06 is reacted with (S)-2-amino-4-methylene-pentanedioc acid dimethyl ester hydrochloride, 1-(3-dimethylaminopropyl)-3-ethyl carbodiimide hydrochloride, 1-hydroxybenzotriazole, and 4-dimethylaminopyridine in a suitable solvent, such as dimethylformamide, in the presence of a hindered base, such as N,N'-diisopropylethylamine. This reaction results in formation of compound I-07 in the desired enantiomeric form (i.e., the (S) enantiomer). Preferably, the remaining reaction steps are carried out in a manner to preserve this stereochemistry. In step 8, (S)-2-{4-[2-(2,4-diamino-quinazolin-6-yl)-ethyl]benzoylamino}-4-methylene-pentanedioic acid dimethyl ester (compound I-07) is reacted with a base in a suitable solvent, such as acetonitrile to form the corresponding dioic acid of compound I-08. In step 9, the salt compound I-09 is formed by forming a solution using an appropriate solvent, such as methanol, and adding an appropriate base providing the desired cation, such as sodium hydroxide. The salt compound can then be precipitated by conventional means. In one embodiment, the foregoing method can be used to prepare a compound according to Formula (12) as a disodium salt or dipotassium salt having an enantiomeric purity of 99.8% for the (S) enantiomer. Specific compounds that may be encompassed by the Formula (6) through Formula (12) and that may be useful according to the invention are disclosed in U.S. Pat. No. 5,912,251, U.S. Pat. No. 7,829,708, U.S. Patent Application Publication No. 2009/0253719, U.S. Patent Application Publication No. 2009/0253720, U.S. Patent Application Publication No. 2011/0112126, U.S. Patent Application Publication No. 2011/0124650, and U.S. Patent Application Publication No. 2011/0237609, the disclosures of which are incorporated herein by reference in their entireties.

In certain embodiments, the active agent combinations of the present invention particularly can comprise the compound methotrexate, or a derivative thereof, in combination with one or more antifolate compounds described above in relation to Formula (6) through Formula (12). In other embodiments, the active agent combinations can comprise methotrexate, or a derivative thereof, in combination with one or more antifolate compounds described above in relation to Formula (6) through Formula (12) and one or more further compounds known to have therapeutic properties. Exemplary further compounds may be toxicity-reducing compounds (e.g., folic acid or leucovorin), anti-inflammatory compounds, anti-arthritic compounds, antibiotics, antifungals, or antiviral agents.

It has particularly been found according to the present invention that the combinations described herein can be effective when delivered to a subject according to a defined dosing regimen. In certain embodiments, the combination of active agents provided according to the present invention are provided such that a first active compound is provided according to a first dosing schedule and at least a second active compound is provided according to a second dosing schedule. Preferably, the first and second dosing schedules differ in one or more of the timing of administration of each of the active compounds, the total number of doses of each active agent administered over a defined time frame (e.g., total number of doses per day, total number of doses per week, total number of doses per month, or total number of doses administered during a customized time frame, such as a defined number of days), or the absolute number of doses administered in a defined treatment interval. In some embodiments, the difference in the dosing schedules may be defined in terms of a ratio of the number of doses of one active compound to the number of doses of another active compound. Such ratio would be understood to cover a sufficient period of administration (e.g., number of days, weeks, or months) such that the value would be mathematically relevant.

The provision of the combination of active agents in the defined dosing regimen can be related to methods of treatment as well as methods of manufacture, such as kits and the like. For example, in some embodiments, the invention can comprise methods of treating a subject by administering a combination of at least two active compounds as described herein. A first active compound can be administered according to a first dosing schedule, and a second compound can be administered according to a second, different dosing schedule. Even further active compounds can be administered, and such compounds could be administered according to one of the aforementioned dosing schedules or according to one or more different dosing schedules. The dosing schedules used in the methods of treatment may comprise daily dosing of at least one of the active compounds administered in the dosing regimen. For example, an active compound may be administered once daily, twice daily, three times daily, or even four times daily, as necessary to achieve a desired treatment effect and/or to accommodate specific pharmacokinetic properties of the active compound and/or effects of the administration specific to a certain subject. The dosing schedules used in the methods of treatment further may comprise weekly dosing of at least one of the active compounds administered in the dosing regimen. For example, an active compound may be administered once weekly, twice weekly, three times weekly, or even four times weekly. Of course, it is understood that when multiple weekly doses are administered, the multiple doses are administered on different days. Similarly, a dosing schedule could comprise administration of a dose once every specific number of days (e.g., one dose every other day, one dose every third day, one dose every fourth day, one dose every fifth day, or one dose every sixth day). Dosing of one or more of the active compounds can be according to an intermittent administration schedule, as otherwise described herein. In such embodiments, it is preferable that the compound being dosed intermittently be administered for at least two consecutive days followed by the prescribed time of discontinuance prior to continuing administration.

In further embodiments, the invention can comprise methods of manufacture, such as kits, that provide a sufficient number of doses of each of the active compounds provided by the combination such that the active compounds (which may be provided in the form of different pharmaceutical formulations) are dosed in the defined regimen. Such articles of manufacture may be formed such that the active compounds may be provided in a sufficient number of dosages to meet any of the dosing schedules described herein (e.g., daily dosing schedule, weekly dosing schedules, or other customized dosing schedules). In certain embodiments, the articles of manufacture particularly may provide the active compounds in a defined number of dosages of each active compound (e.g., individual dosages of the active compounds, such as in the form of pharmaceutical formulations) such that the dosages of the active compounds are in a defined ratio. For example, a kit according to the invention could include a sufficient number of dosages of a first pharmaceutical composition including a first active compound and a second pharmaceutical composition including a second active compound such that the compositions are dosed in a regimen of at least "X" number of doses of the first composition for each "Y" number of doses of the second composition. In specific embodiments (e.g., where two active compounds are provided in two different pharmaceutical compositions), a kit could provide a sufficient number of each composition such that they can be dosed in a regimen of at least 2:1 (i.e., at least two doses of one composition per single dose of the other composition), at least 3:1, at least 4:1, at least 5:1, at least 6:1, at least 7:1, at least 8:1, at least 9:1, at least 10:1, at least 11:1, at least 12:1, at least 13:1, at least 14:1, at least 15:1, at least 16:1, at least 17:1, at least 18:1, at least 19:1, at least 20:1, at least 21:1, at least 22:1, at least 23:1, at least 24:1, at least 25:1, at least 26:1, at least 27:1, at least 28:1, at least 29:1, or at least 30:1. For example, in the above ratios, the composition provided for the higher dosing regimen of the combination may relate to an antifolate compound described herein in relation to Formula (6) through Formula (12), and the composition provided for the lower dosing regimen of the combination may relate to methotrexate. If more than two compositions with more than two active compounds are provided, the ratio can be expanded to accommodate the further active compounds and the specific ratios in which the dosages are provided (e.g., and "A" to "B" to "C" ratio where three active compounds are provided, such as in three different pharmaceutical compositions).

Such ratio of dosages can encompass dosing regimens wherein one active compound is administered on a different time basis than another active compound (e.g., one compound administered daily and the other compound administered weekly). For example, dosages could be provided in an amount sufficient such that they are dosed in a regimen of at least one dose per day of one active compound (or its pharmaceutical composition) for each one dose per week of another active compound (or its pharmaceutical composition). Any combination of doses could be provided to provide one dose per day to about four doses per day of one active compound (or its pharmaceutical composition) for each one dose per week to about 4 doses per week of another active compound (or its pharmaceutical composition). Such values could be easily adjusted such that the dosages for each compound (or pharmaceutical composition) are both identified on a daily basis, a weekly basis, or even a monthly basis.

The ratios also can encompass absolute values. For example, a kit according to the invention could comprise a sufficient number of doses of each active compound provided in the combination to accommodate any of the embodiments provided herein, and the number of doses could be allocated on a specific time basis. For example, the article of manufacture could provide a sufficient number of dosages to provide a dosing regimen that covers a single week. In such embodiments, the article of manufacture could comprise about seven to about 28 doses of one active compound (or its pharmaceutical composition) and one to about four doses of another active compound (or its pharmaceutical composition). The article of manufacture similarly could provide a sufficient number of dosages to provide a dosing regimen that covers a single month. In such embodiments, the article of manufacture could comprise about 30 to about 120 doses of one active compound (or its pharmaceutical composition) and one to about 16 doses of another active compound (or its pharmaceutical composition). Even further dosing regimens can be envisioned in relation to the specific examples provided herein and the further description provided herein in relation to specific embodiments of active compound combinations, and all such dosing regimens are understood to be encompassed by the present invention.

As noted above, active compounds of the present invention may be provided in pharmaceutical compositions. Further, the combined active compounds can be prepared and delivered in a variety of forms. For example, a single composition containing all of the active ingredients may be provided. In specific embodiments, the active agents are provided in multiple compositions comprising separate active ingredients but intended to be administered in a defined dosing regimen, as further described herein.

The pharmaceutical compositions can be prepared to deliver one or more active agents described herein together with one or more pharmaceutically acceptable carriers therefore, and optionally, other therapeutic ingredients. Carriers should be acceptable in that they are compatible with any other ingredients of the composition and not harmful to the recipient thereof. A carrier may also reduce any undesirable side effects of the agent. Non-limiting examples of carriers that could be used according to the invention are described by Wang et al. (1980) *J. Parent. Drug Assn.* 34(6):452-462, herein incorporated by reference in its entirety.

The combinations of the invention preferably provide an active agent as described herein in a therapeutically effective amount, as further described below. In certain embodiments, the amount of the active agent can be based on the overall weight of a composition in which it is provided. For example, in certain embodiments, a pharmaceutical composition can comprise an active agent as described herein in an amount of about 0.01 mg/g to about 100 mg/g. In further embodiments, the pharmaceutical composition can comprise an active agent as described herein in an amount of about 0.02 mg/g to about 80 mg/g, about 0.05 mg/g to about 75 mg/g, about 0.08 mg/g to about 50 mg/g, about 0.1 mg/g to about 30 mg/g, about 0.25 mg/g to about 25 mg/g, or about 0.5 mg/g to about 20 mg/g. The amount of drug can also be referenced to a unit dose (e.g., the amount of drug in a single capsule or tablet). The content of the active agent can be referenced to the content of a salt form or other form of the compound used in the composition. In other embodiments, even when a specific form is used, the amount of the active agent can be referenced to the content of the basic compound form (e.g., a free acid form) that is present.

Compositions useful according to the invention may include short-term, rapid-onset, rapid-offset, controlled release, sustained release, delayed release, and pulsatile release compositions, providing the compositions achieve administration of a compound as described herein. See *Remington's Pharmaceutical Sciences* (18$^{th}$ ed.; Mack Publishing Company, Eaton, Pa., 1990), herein incorporated by reference in its entirety.

Pharmaceutical compositions according to the present invention are suitable for various modes of delivery, including oral, parenteral (including intravenous, intramuscular, subcutaneous, intradermal, intra-articular, intra-synovial, intrathecal, intra-arterial, intracardiac, subcutaneous, intraorbital, intracapsular, intraspinal, intrasternal, and transdermal), topical (including dermal, buccal, and sublingual), pulmonary, vaginal, urethral, and rectal administration. Administration can also be via nasal spray, surgical implant, internal surgical paint, infusion pump, or via catheter, stent, balloon or other delivery device. The most useful and/or beneficial mode of administration can vary, especially depending upon the condition of the recipient and the disorder being treated. In preferred embodiments, the compositions of the present invention are provided in an oral dosage form, as more fully described below.

The pharmaceutical compositions may be conveniently made available in a unit dosage form, whereby such compositions may be prepared by any of the methods generally known in the pharmaceutical arts. Generally speaking, such methods of preparation comprise combining (by various methods) the active compounds of the invention with a suitable carrier or other adjuvant, which may consist of one or more ingredients. The combination of the active ingredients with the one or more adjuvants is then physically treated to present the composition in a suitable form for delivery (e.g., shaping into a tablet or forming an aqueous suspension).

Adjuvants or accessory ingredients, in addition to those discussed above, for use in the compositions of the present invention can include any pharmaceutical ingredient commonly deemed acceptable in the art, such as binders, fillers, lubricants, disintegrants, diluents, surfactants, stabilizers, preservatives, flavoring and coloring agents, and the like. Binders are generally used to facilitate cohesiveness of the tablet and ensure the tablet remains intact after compression. Suitable binders include, but are not limited to: starch, polysaccharides, gelatin, polyethylene glycol, propylene glycol, waxes, and natural and synthetic gums. Acceptable fillers include silicon dioxide, titanium dioxide, alumina, talc, kaolin, powdered cellulose, and microcrystalline cellulose, as well as soluble materials, such as mannitol, urea, sucrose, lactose, dextrose, sodium chloride, and sorbitol. Lubricants are useful for facilitating tablet manufacture and include vegetable oils, glycerin, magnesium stearate, calcium stearate, and stearic acid. Disintegrants, which are useful for facilitating disintegration of the tablet, generally include starches, clays, celluloses, algins, gums, and crosslinked polymers. Diluents, which are generally included to provide bulk to the tablet, may include dicalcium phosphate, calcium sulfate, lactose, cellulose, kaolin, mannitol, sodium chloride, dry starch, and powdered sugar. Surfactants suitable for use in the composition according to the present invention may be anionic, cationic, amphoteric, or nonionic surface active agents. Stabilizers may be included in the compositions to inhibit or lessen reactions leading to decomposition of the active agents, such as oxidative reactions.

Delivery of a therapeutically effective amount of each of the active agents used in the inventive combinations may be obtained via administration of a therapeutically effective dose of each active agent. Accordingly, in certain embodiments, a therapeutically effective amount is an amount effective to treat an inflammation related condition. In more specific embodiments, a therapeutically effective amount is an amount effective to treat an arthritic condition. In yet further embodiments, a therapeutically effective amount is an amount effective to treat rheumatoid arthritis.

The active compounds are provided in the combinations in amounts sufficient to deliver to a patient a therapeutic amount of the compounds in vivo in the absence of serious toxic effects. The concentrations of the active compounds in the combinations will depend on absorption, inactivation, and excretion rates of the drug as well as other factors known to those of skill in the art. It is to be noted that dosage values also can vary with the severity of the condition to be alleviated. It is to be further understood that for any particular subject, specific dosage regimens may be adjusted over time according to the individual need and the professional judgment of the person administering or supervising the administration of the compositions, and that the dosage ranges set forth herein are exemplary only and are not intended to limit the scope or practice of the invention.

A therapeutically effective amount according to the invention can be determined based on the bodyweight of the recipient. For example, in one embodiment, a therapeutically effective amount of one or more compounds of the invention is in the range of about 0.1 µg/kg of body weight to about 5 mg/kg of body weight per day. Alternatively, a therapeutically effective amount can be described in terms of a fixed dose. Therefore, in another embodiment, a therapeutically effective amount of one or more compounds of the invention is in the range of about 0.01 mg to about 500 mg per dose. Of course, it is understood that such an amount could be divided into a number of smaller dosages administered throughout the day. The effective dosage range of pharmaceutically acceptable salts and prodrugs can be calculated based on the weight of the parent compound to be delivered. If a salt or prodrug exhibits activity in itself, the effective dosage can be estimated as above using the weight of the salt or prodrug, or by other means known to those skilled in the art.

In some embodiments, an effective amount of methotrexate according to the present invention can be characterized in relation to total amount administered on a weekly basis. For example, an effective amount of methotrexate can be at least about 0.1 mg/week, at least about 0.5 mg/week, at least about 1 mg/week, at least about 2 mg/week, at least about 5 mg/week, at least about 10 mg/week, at least about 15 mg/week, at least about 20 mg/week, or at least about 25 mg/week. In further embodiments, an effective amount of methotrexate can be about 1 to about 50 mg/week, about 2 to about 40 mg/week, about 3 to about 35 mg/week, about 4 to about 30 mg/week, or about 5 to about 25 mg/week, about 5 to about 20 mg/week, or about 5 to about 15 mg/week. This amount can be provided as a single dose (i.e., one dose per week) or can be divided into multiple doses as otherwise described herein (e.g., two, three, four, five, or six doses per week). In some embodiments, dosing of methotrexate may be referred to as low dose administration, and such terminology can refer to the significantly reduced dosing of methotrexate required in the combination of the present invention in relation to dosing of methotrexate alone. In some embodiments, low dose methotrexate administration can refer to dosing in an amount of less than about 100 mg/week, less than about 90 mg/week, less than about 80 mg/week, less than about 70 mg/week, less than about 60 mg/week, or less than about 50 mg/week. Of course, it is understood that such ranges require some minimum amount of methotrexate being administered. Such low dose administration of methotrexate can particularly be achieved in light of the combination with the further antifolate compounds described herein. Thus, as otherwise described herein, a synergistic effect may be realized such that excellent effects can be achieved by using a lower dose of methotrexate than would be expected to achieve the same therapeutic effect.

In certain embodiments, an effective amount of an antifolate compound according to the present invention [e.g., a compound according to any one of Formulas (6) through (12)] can be characterized in relation to total amount administered on a daily basis. For example, an effective amount of such compounds can be at least about 0.01 mg/day, at least about 0.05 mg/day, at least about 0.1 mg/day, at least about 0.2 mg/day, or at least about 0.3 mg/day. In further embodiments, an effective amount of such compounds can be about 0.05 to about 20 mg/day, about 0.1 to about 15 mg/day, about 0.1 to about 10 mg/day, about 0.1 to about 8 mg/day, about 0.1 to about 7 mg/day, about 0.1 to about 5 mg/day, about 0.1 to about 4 mg/day, about 0.1 to about 3 mg/day, about 0.2 to about 3 mg/day, about 0.25 to about 2 mg/day, or about 0.3 to about 1 mg/day. Doses in the lower ends of the noted ranges may be used when the compounds are administered on a daily basis with no periods of discontinued use. In embodiments where intermittent administration may be used, doses in the higher ends of the noted ranges may be used. For example, if the compounds were given with one, two, three, or even more days off in between dosings, the dosing on days of administration may be in the range of about 5 to about 20 mg/day, about 5 to about 15 mg/day, about 5 to about 12 mg/day, or about 5 to about 10 mg/day.

It is contemplated that the combinations of the invention will be administered in therapeutically effective amounts to a mammal, preferably a human. An effective dose of a compound for treatment of any of the conditions or diseases described herein can be readily determined by the use of conventional techniques and by observing results obtained under analogous circumstances. The effective amount of the combinations would be expected to vary according to the weight, sex, age, and medical history of the subject. Of course, other factors could also influence the effective amount of the combination to be delivered, including, but not limited to, the specific disease involved, the degree of involvement or the severity of the disease, the response of the individual patient, the particular compound administered, the mode of administration, the bioavailability characteristics of the preparation administered, the dosing regimen selected, and the use of concomitant medication. The compound is preferentially administered for a sufficient time period to alleviate the undesired symptoms and the clinical signs associated with the condition being treated. Methods to determine efficacy and dosage are known to those skilled in the art. See, for example, Isselbacher et al. (1996) *Harrison's Principles of Internal Medicine* 13 ed., 1814-1882, herein incorporated by reference.

In certain embodiments, the present invention particularly provides methods for treating a subject suffering from specific conditions. In particular, the inventive combinations may be used in methods for treating a subject suffering from an inflammation related condition—i.e., diseases characterized by inflammation. Diseases and conditions which have significant inflammatory components are ubiquitous and include, for example, skin disorders, bowel disorders, certain degenerative neurological disorders, arthritis, autoimmune diseases and a variety of other illnesses. Some of these diseases have both an inflammatory and proliferative component. Thus, the invention can be particularly beneficial in that the combination of compounds can provide anti-inflammatory and anti-proliferative activity. In particular embodiments the inventive combinations of compounds can be used to treat conditions such as arthritis (e.g., rheumatoid arthritis), inflammatory bowel diseases (IBD), Crohn's disease (CD), ulcerative colitis (UC), chronic obstructive pulmonary disease (COPD), sarcoidosis, psoriasis, allergic disorders, skin disorders, transplant rejection, poststreptococcal and autoimmune renal failure, septic shock, systemic inflammatory response syndrome (SIRS), adult respiratory distress syndrome (ARDS), envenomation, lupus erythematosus, Hashimoto's thyroiditis, autoimmune hemolytic anemias, insulin dependent diabetes mellitus, and rheumatic fever, pelvic inflammatory disease (PID), conjunctivitis, dermatitis, and bronchitis.

The combinations of the invention particularly can be useful in the treatment of arthritis related conditions. More than 40 million Americans suffer from arthritis in its various forms, including over 100 kinds of rheumatic diseases (i.e., diseases affecting joints, muscle, and connective tissue, which makes up or supports various structures of the body, including tendons, cartilage, blood vessels, and internal organs). Representative types of arthritis include rheumatoid (such as soft-tissue rheumatism and non-articular rheumatism), fibromyalgia, fibrositis, muscular rheumatism, myofascil pain, humeral epicondylitis, frozen shoulder, Tietze's syndrome, fascitis, tendinitis, tenosynovitis, bursitis, juvenile chronic, spondyloarthropaties (ankylosing spondylitis), osteoarthritis, hyperuricemia and arthritis associated with acute gout, chronic gout, and systemic lupus erythematosus.

In specific embodiments, the inventive combinations are particularly useful in the treatment of rheumatoid arthritis, which is an autoimmune disease that can affect the whole body, causing weakness, fatigue, loss of appetite, and muscle pain. Typically, the age of onset is much earlier than osteoarthritis, between ages 20 and 50. Inflammation begins in the synovial lining and can spread to the entire joint.

In certain embodiments, the invention can provide method methods for treating a subject suffering from an inflammation related condition. Specifically, the methods can comprise administering a polyglutamylatable antifolate compound (such as methotrexate) in combination with an antifolate compound according to Formula (6) through Formula (12). In preferred embodiments, the compounds can be administered in specific dosing schedules, as described herein.

As described in the experimental section below, the inventive combinations of the invention, particularly the combination of methotrexate and any of the antifolate compounds according to Formula (6) through Formula (12), can be especially useful in the treatment of rheumatoid arthritis. Although not wishing to be bound by theory, it is believed that the inventive combination are particularly useful (and may even be described as acting synergistically) because the combination of compounds can work through different mechanisms. For example, the compounds of Formula (6) through Formula (12) are non-polyglutamylatable and thus can function as a pure DHFR inhibitor (as described below), while methotrexate works through inactivation of alternate enzymes following polyglutamylation. Specifically, methotrexate acts on multiple enzymes, including aminoimidazole carboxamide ribonucleotide (AICAR), thymidylate synthetase (TS), dihydrofolate reductase (DHFR), and glycinamide ribonucleotide formyltransferase (GARFT).

Aminoimidazole carboxamide ribonucleotide is an intermediate in the generation of inosine monophosphate, which acts as an AMP-activated protein kinase agonist. It stimulates glucose uptake and increases the activity of p38 mitogen-activated protein kinases α and β in skeletal muscle tissue, as well as suppressing apoptosis by reducing production of reactive oxygen compounds inside the cell Thymidylate synthase is a rate-limiting enzyme in pyrimidine de novo deoxynucleotide biosynthesis and is therefore often a target for chemotherapeutic strategies. In DNA synthesis, TS plays a central role in reductive methylation of deoxyuridine-5'-monophosphate (dUMP) to deoxythymidine-5'-monophosphate (dTMP). Thus, TS inhibition leads directly to depletion of dTMP and subsequently of 2'-deoxythymidine-5'-triphosphate (dTTP), an essential precursor for DNA. This indirectly results in an accumulation of 2'-deoxyuridine-5'-triphosphate (dUTP) and, therefore, leads to so-called "thymine-less death" due to misincorporation of dUTP into DNA and subsequent excision catalyzed by uracil-DNA glycosylase, which causes DNA damage. Both this DNA damage and the noted imbalance in dTTP/dUTP can induce downstream events, leading to apoptosis (cell death).

Dihydrofolate reductase catalyzes the NADPH-dependent reduction of 7,8-dihydrofolate (DHF or H2F) to 5,6,7,8-tetrahydrofolate (THF or H4F). Thus, DHFR is necessary for maintaining intracellular levels of THF, an essential cofactor in the synthetic pathway of purines, thymidylate, and several amino acids.

Glycinamide ribonucleotide formyltransferase (GARFT) is a folate-dependent enzyme in the de novo purine biosynthesis pathway critical to cell division and proliferation. Specifically, GARFT catalyzes the formation of purines from the reaction of 10-formyltetrahydrofolate (10-FTHF) to THF Inhibition of GARFT results in a depletion in intracellular purine levels, which in turn inhibits DNA and RNA synthesis. Ultimately, disruption of DNA and RNA synthesis by GARFT inhibition results in cell death. The antiproliferative effect associated with GARFT inhibition makes it a particularly desirable target for anti-tumor drugs.

Methotrexate can be transported into cells by mechanisms such as the reduced folate carrier system and the membrane folate binding protein transport system. Once in the cell, methotrexate is converted to polyglutamylate forms by folyl polyglutamate synthase. The polyglutamylate forms are retained in cells and are inhibitors of enzymes, such as noted above. Polyglutamylation is a time- and concentration-dependent process that occurs in tumor cells and, to a lesser extent, in normal tissues. Polyglutamylated metabolites have an increased intracellular half-life resulting in prolonged drug action.

Methotrexate can be a highly useful drug in light of its broad action against multiple enzymes. Conversely, it can be undesirable in some cases to administer the compound, particularly in high doses. For example, inhibition of TS and GARFT is strongly related to cell death, thus the desirability of using TS and GARFT inhibitors as anti-tumor drugs. However, the ability of drugs, such as methotrexate, to induce apoptosis increases the toxicity of the drug (i.e., death of healthy cells as well as tumor cells).

The function of compounds, such as methotrexate, as inhibitors of TS and GARFT arises from the polyglutamylation of the compound inside the cell. Accordingly, compounds that are non-polyglutamylatable would not be expected to function as a TS inhibitor or a GARFT inhibitor. However, inhibition of polyglutamylation does not generally affect the ability of a compound to function as a DHFR inhibitor. For example, the compound pemetrexed (which is polyglutamylatable) has been shown to have equivalent DHFR inhibition in comparison to the polyglutamate forms of pemetrexed.

The compounds of Formula (6) through Formula (12) comprise a 4-methylidene group in the glutamate moiety of the compounds. Such may also be referred to as a gamma methylene glutamate moiety. The presence of the methylene group makes the antifolate compounds non-polyglutamylatable. Accordingly, the compounds of Formula (6) through Formula (12) are specific for DHFR inhibition (i.e., do not inhibit TS or GARFT due to the absence of polyglutamylation inside cells). Such specificity is desirable to provide for more specific treatments while avoiding or reducing toxicity and minimizing side-effects more commonly associated with compounds, such as pemetrexed, which act on additional enzymes, such as TS and GARFT.

It has been found according to the present invention that administration of methotrexate in relatively low doses can be effective in treating inflammation related conditions, such as rheumatoid arthritis, while minimizing any undesirable side effects of the drug, as described above. The effectiveness of low dose methotrexate therapy, however, is surprisingly increased by combining the drug with an antifolate compound according to Formula (6) through Formula (12). This surprising result is believed to arise from the recognition that methotrexate treatment provides beneficial effects from the multiple enzyme inhibiting activity of the polyglutamylate form of the compound, while the low dose of the drug minimizes the undesirable effects, and the recognition that the loss in effect by using only a low dose of methotrexate is overcome by the DHFR-specific compounds according to Formula (6) through Formula (12), which provide desirable therapeutic effects of DHFR inhibition without the undesirable effects of enzyme inhibition arising from polyglutamylate forms of other antifolate compounds.

In light of the synergistic effects of the active compound combinations, the present invention in some embodiments can be characterized as providing a method of potentiating the effectiveness of a polyglutamylatable antifolate compound (such as methotrexate) in the treatment of a condition recognized as being treatable with the polyglutamylatable antifolate compound, such as inflammation related conditions. Specifically, the method can comprise administering the polyglutamylatable antifolate compound (such as methotrexate) in combination with an antifolate compound according to Formula (6) through Formula (12).

Potentiation of methotrexate efficacy in treatment of inflammation related conditions (such as rheumatoid arthritis) by combination therapy with a compound of Formula (6) through Formula (12) (i.e., the synergistic effect of the combination) can be characterized by an increase in the actual therapeutic effect being measured relative to the measured therapeutic effect observed with administration of methotrexate alone. In specific embodiments, potentiation of methotrexate efficacy can be characterized by an increase in therapeutic effect of at least about 10%, at least about 20%, at least about 30%, at least about 40%, at least about 50%, at least about 60%, at least about 70%, at least about 80%, at least about 90%, or at least about 100%. Of course, it is understood that when the therapeutic effect corresponds to a decrease in a measurable marker or a decrease in the severity of a specific symptom, the above-noted percentages would likewise correlate to the described decrease in the measurable marker or the decrease in the severity of the specific symptom. Non-limiting examples of markers that may be illustrative of improvement in symptoms achieved according to the present invention include decreased levels of inflammatory cytokines, antibodies, citrulinated proteins, reactive T-lymphocytes (CD4 or CD8), and the like. The benefits of the invention further may be exemplified in relation to particular models, such as decreased swelling of affected joints, decreased immune cell infiltration, destruction of bone and/or cartilage, and pannus formation in affected joints in animal models.

In light of the foregoing, it can be seen that the invention encompasses a method of potentiating the effectiveness of methotrexate in the treatment of rheumatoid arthritis (e.g., providing a synergistic effect by the combination of the compounds), the method comprising administering methotrexate or a derivative thereof to a patient suffering from rheumatoid arthritis in combination with an antifolate compound according to Formula (6):

(6)

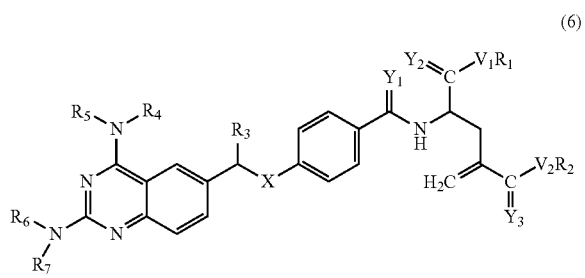

wherein:

X is $CHR_8$ or $NR_8$;

$Y_1$, $Y_2$, and $Y_3$ independently are O or S;

$V_1$ and $V_2$ independently are O, S, or NZ;

Z is H, optionally substituted alkyl, optionally substituted alkenyl, optionally substituted alkynyl, or alkaryl;

$R_1$ and $R_2$ independently are H, optionally substituted alkyl, optionally substituted alkenyl, optionally substituted alkynyl, or alkaryl;

$R_3$ is H, optionally substituted alkyl, optionally substituted alkenyl, optionally substituted alkynyl, optionally substituted alkoxy, hydroxyl, or halo; and $R_4$, $R_5$, $R_6$, $R_7$, and $R_8$ independently are H, optionally substituted alkyl, optionally substituted alkenyl, optionally substituted alkynyl, acyl, —C(O)-alkyl, —C(O)-alkenyl, or —C(O)-alkynyl; or a pharmaceutically acceptable ester, amide, salt, solvate, enantiomer, or prodrug thereof;

wherein the effectiveness of the treatment is improved in relation to treatment with methotrexate alone.

In certain embodiments, the antifolate compound particularly can be a compound according to formula (7):

(7)

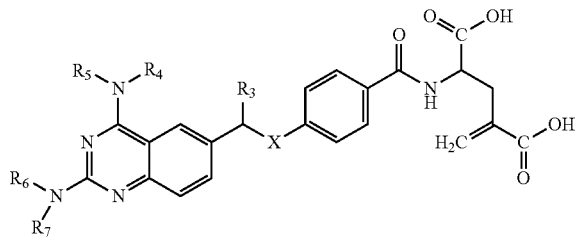

wherein:

X is $CHR_8$ or $NR_8$;

$R_3$ is H, optionally substituted alkyl, optionally substituted alkenyl, optionally substituted alkynyl, optionally substituted alkoxy, hydroxyl, or halo; and $R_4$, $R_5$, $R_6$, $R_7$, and $R_8$ independently are H, optionally substituted alkyl, optionally substituted alkenyl, optionally substituted alkynyl, acyl, —C(O)-alkyl, —C(O)-alkenyl, or —C(O)-alkynyl; or a pharmaceutically acceptable ester, amide, salt, solvate, enantiomer, or prodrug thereof. In specific embodiments, the antifolate compound can be a compound according to Formula (9):

(9)

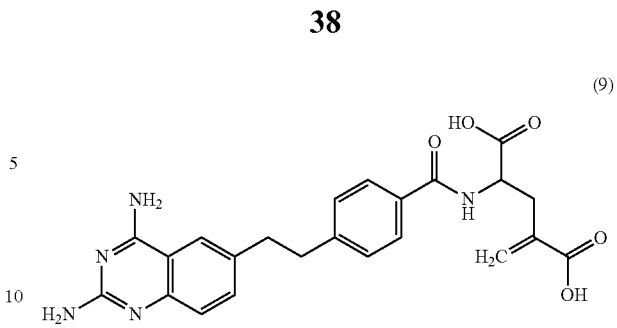

or a pharmaceutically acceptable ester, amide, salt, solvate, enantiomer, or prodrug thereof. Still further, the antifolate compound can be a compound according to Formula (11):

(11)

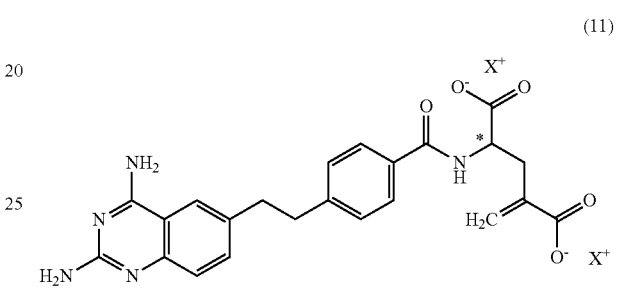

or an enantiomer thereof, wherein each $X^+$ independently is a salt-forming counterion. In such embodiments, $X^+$ can be an alkali metal cation—e.g., sodium or potassium. Preferably, the antifolate compound can be a crystalline salt, more particularly a racemic salt. In some embodiments, the antifolate compound can be a compound according to Formula (12):

(12)

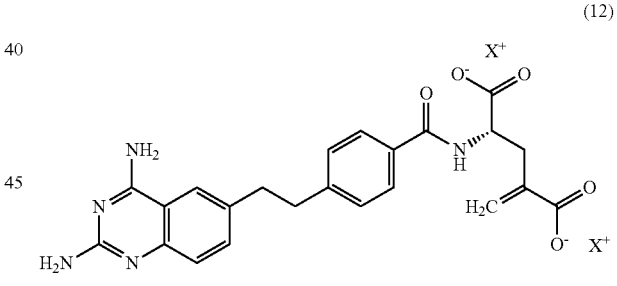

wherein each $X^+$ independently is a salt-forming counterion, and wherein the antifolate compound is in the (S) enantiomeric form. Specifically, the antifolate compound can exhibit an enantiomeric purity for the (S) enantiomer of at least about 90%, at least about 95%, or at least about 99%. In one embodiment, the antifolate compound can be a compound according to Formula (12) that is a crystalline, disodium salt in the (S) enantiomeric form exhibiting an enantiomeric purity for the (S) enantiomer of at least about 99%. Further, the antifolate compound can be a compound according to Formula (12) that is a crystalline, dipotassium salt in the (S) enantiomeric form exhibiting an enantiomeric purity for the (S) enantiomer of at least about 99%.

In addition to the above-described methods, the present invention also can provide articles of manufacture for packaging, storing, and/or delivering the inventive combinations of active compounds. Particularly, the articles of manufacture can be characterized by the ability to provide the active compounds in forms, dosages, and doses appropriate for a defined dosing regimen, as described herein. The article of manufacture can include a container that contains the active compounds in dosage forms suitable for use according to the present invention together with any carrier, either dried or in liquid form. For example, the invention can comprise a kit including multiple dosages, each comprising one or more active compounds, the dosages being intended for administration in combination, in succession, or in other relationship, as described herein. The dosages could be solid forms (e.g., tablets, caplets, capsules, or the like) or liquid forms (e.g., vials), each comprising a single active compound. The dosage forms could be provided in blister packs, bags, or the like, for administration in combination. The kit can comprise a container in any conventional shape or form as known in the art, for example, a paper box, a glass or plastic bottle, or a blister pack, tray, or card with individual dosage forms being individually dispensible in single doses—e.g., such as by pressing out of the back of a blister pack or card or being individually wrapped and withdrawn from a tray according to a defined therapeutic schedule or dosing regimen, as described herein.

The article of manufacture further can include instructions in various forms for the carrying out the method of the invention. For example, the instructions may be in the form of a label on the container and/or in the form of an insert included in a box in which the container is packaged, and/or in step-by-step instructions printed directly on a blister pack, punch card, or the like. The instructions can also be printed on a box or other packaging in which the vial, blister pack, or the like is packaged. The instructions preferably can contain information such as sufficient dosage and administration information so as to allow the subject or a worker in the field to administer the combination of compounds according to the defined dosing regimen. It is anticipated that a worker in the field encompasses any doctor, nurse, technician, spouse, or other caregiver that might administer the composition. The combination of active compounds can also be self-administered by the subject.

EXPERIMENTAL

The present invention will now be described with specific reference to the following example, which is not intended to be limiting of the invention and is rather provided to show exemplary embodiments. In the specific testing described below, the term "CH-4051" specifically is the compound of Formula (12), wherein both $X^+$ are potassium, and the label "MTX" refers to the compound methotrexate.

Example

Effects of CH-4051 and Methotrexate, Alone and in Combination, in Treatment of Rat Model of Polyarthritis Rat collagen arthritis is an experimental model of polyarthritis that has been widely used for preclinical testing of numerous anti-arthritic agents that are either under preclinical or clinical investigation or are currently used as therapeutics in this disease (see Trentham, D. E., et al., 1977, "Autoimmunity to type II collagen: an experimental model of arthritis", *J. Exp. Med.*, pp. 857-868; Bendele A. M., et al., 1999, "Animal models of arthritis: relevance to human disease", *Toxicologic Pathol.*, 27: pp. 134-242; and Bendele A. M., 2001, "Animal Models of Rheumatoid Arthritis", *J. Musculoskel. Interact.*, pp. 377-385, all of which are incorporated herein by reference). The hallmarks of this model are: reliable onset and progression of robust, easily measurable, polyarticular inflammation; marked cartilage destruction in association with pannus formation; and mild to moderate bone resorption and periosteal bone proliferation. Therapeutic agents that inhibit interleukin-1 (IL-1) production or activity are especially active in this test system, but other types of anti-inflammatory agents have good to excellent activity.

Testing described below was carried out to determine the effects of CH-4051 and methotrexate, alone and in combination, for inhibition of the inflammation (e.g., paw swelling), cartilage destruction, and bone resorption that occurs in developing type II collagen arthritis in rats. Female Lewis rats (n=74) weighing 140-161 grams (mean approximate weight=148 g) on day 0 of the study were obtained from Charles River Laboratories, Inc., Wilmington, Mass. Animals were identified by a distinct number delineating group and animal number. After randomization, all cages were labeled with protocol number, group number, and animal number with appropriate color-coding.

Animals were anesthetized with Isoflurane and received subcutaneous/intradermal (SC/ID) injections with 300 µA of Freund's Incomplete Adjuvant (Difco, Detroit, Mich.) containing 2 mg/ml bovine type II collagen (Elastin Products, Owensville, Mo.) at the base of the tail and two sites on the back on days 0 and 6. Dosing was initiated on day 0 of the study (prior to boosting procedures) and continued daily (QD at 24 hour intervals) through day 16. Animals were terminated on day 17. The experimental groups were as follows in Table 1, wherein "CH vehicle" means the vehicle used to deliver the compound CH-4051 without the inclusion of the active compound, and "MTX vehicle" means the vehicle used to deliver methotrexate without the inclusion of the active compound. The terms "QD" and "PO" have the standard meanings in the art—i.e., "once daily" and "by mouth", respectively.

TABLE 1

| Group | N | Treatment (5 ml/kg QD PO dosing, days 0-16) |
|---|---|---|
| 1 | 4 | Normal controls, CH vehicle daily, MTX vehicle 2X/week |
| 2 | 10 | Arthritis + CH vehicle daily, MTX vehicle 2X/week |
| 3 | 10 | Arthritis + CH vehicle daily, MTX 0.1 mg/kg 2X/week |
| 4 | 10 | Arthritis + CH-4051 daily 2.5 mg/kg, MTX vehicle 2X/week |
| 5 | 10 | Arthritis + CH-4051 daily 2.5 mg/kg, MTX 0.1 mg/kg 2X/week |
| 6 | 10 | Arthritis + CH vehicle daily, MTX 0.2 mg/kg 2X/week |
| 7 | 10 | Arthritis + CH-4051 daily 5 mg/kg, MTX vehicle 2X/week |
| 8 | 10 | Arthritis + CH-4051 daily 5 mg/kg, MTX 0.2 mg.kg 2X/week |

Rats were weighed on days 0, 3, 6, and 9-17 of the study, and caliper measurements of ankles were taken every day beginning on day 9 (or day 0 of arthritis). Ankle caliper measurements were made with Digitrix II micrometer (Fowler & NSK). Baseline measurements were taken using one ankle with values rounded to one-thousandth of an inch. Measurements were confirmed as clinically normal (0.260-0.264 inches) by comparison with historical values for rats based on a range of body weights. Baseline measurements were then applied to both ankles, and these values remained with the animal so long as the ankle was clinically normal with good definition of all the ankle bones and no evidence of inflammation.

After final body weight measurement on day 17, animals were anesthetized for terminal serum collection (retained), and then euthanized for tissue collection. Hind paws were transected at the level of the medial and lateral malleolus, weighed, and were placed in formalin with knees for potential microscopy. Livers, spleen, and thymus were removed, trimmed, weighed, and discarded.

Preserved and decalcified (5% formic acid) ankle and knee joints were cut in half longitudinally (ankles) or in the frontal plane (knees), processed through graded alcohols and a clearing agent, infiltrated and embedded in paraffin, sectioned, and stained with Toluidine Blue (T. blue) by Bolder BioPATH, Inc. associated personnel (HistoTox Labs, Inc.). Tissues from all animals were examined microscopically by a board certified veterinary pathologist, and observations were entered into a computer-assisted data retrieval system. Collagen arthritic ankles and knees were given scores of 0-5 for inflammation, pannus formation, and bone resorption according to the criteria provided below in Table 2 through Table 9.

TABLE 2

| Score | Knee and Ankle Inflammation |
| --- | --- |
| 0 | Normal |
| 1 | Minimal infiltration of inflammatory cells in synovium/periarticular tissue |
| 2 | Mild infiltration |
| 3 | Moderate infiltration with moderate edema |
| 4 | Marked infiltration with marked edema |
| 5 | Severe infiltration with severe edema |

TABLE 3

| Score | Ankle Pannus |
| --- | --- |
| 0 | Normal |
| 1 | Minimal infiltration of pannus in cartilage and subchondral bone, primarily affects marginal zones |
| 2 | Mild infiltration (<¼ of tibia or tarsals at marginal zones) |
| 3 | Moderate infiltration (¼ to ⅓ of tibia or small tarsals affected at marginal zones) |
| 4 | Marked infiltration (½ to ¾ of tibia or tarsals affected at marginal zones) |
| 5 | Severe infiltration (>¾ of tibia or tarsals affected at marginal zones, severe distortion of overall architecture) |

TABLE 4

| Score | Knee Pannus |
| --- | --- |
| 0 | Normal |
| 1 | Minimal infiltration of pannus in cartilage and subchondral bone, approximately 1-10% of cartilage surface or subchondral bone affected |
| 2 | Mild infiltration (extends over up to ¼ of surface or subchondral area of tibia or femur), approximately 11-25% of cartilage surface or subchondral bone affected |
| 3 | Moderate infiltration (extends over >¼ but less than ½ of surface or subchondral area of tibia or femur), approximately 26-50% of cartilage surface or subchondral bone affected |
| 4 | Marked infiltration (extends over ½ to ¾ of tibial or femoral surface), approximately 51-75% of cartilage surface or subchondral bone affected |
| 5 | Severe infiltration, approximately 76-100% of cartilage surface or subchondral bone affected |

TABLE 5

| Score | Ankle Cartilage Damage (emphasis on small tarsals) |
| --- | --- |
| 0 | Normal |
| 1 | Minimal to mild loss of toluidine blue staining with no obvious chondrocyte loss or collagen disruption |

TABLE 5-continued

| Score | Ankle Cartilage Damage (emphasis on small tarsals) |
| --- | --- |
| 2 | Mild loss of toluidine blue staining with focal mild (superficial) chondrocyte loss and/or collagen disruption |
| 3 | Moderate loss of toluidine blue staining with multifocal moderate (depth to middle zone) chondrocyte loss and/or collagen disruption, smaller tarsals affected to ½ to ¾ depth with rare areas of full thickness loss |
| 4 | Marked loss of toluidine blue staining with multifocal marked (depth to deep zone) chondrocyte loss and/or collagen disruption, 1 or 2 small tarsal surfaces have full thickness loss of cartilage |
| 5 | Severe diffuse loss of toluidine blue staining with multifocal severe (depth to tide mark) chondrocyte loss and/or collagen disruption affecting more than 2 cartilage surfaces |

TABLE 6

| Score | Knee Cartilage Damage |
| --- | --- |
| 0 | Normal |
| 1 | Minimal to mild loss of toluidine blue staining with no obvious chondrocyte loss or collagen disruption |
| 2 | Mild loss of toluidine blue staining with focal mild (superficial) chondrocyte loss and/or collagen disruption, may have few small areas of 50% depth of cartilage affected |
| 3 | Moderate loss of toluidine blue staining with multifocal moderate (depth to middle zone) chondrocyte loss and/or collagen disruption, small areas of full thickness loss affecting less than ¼ of the total width of a surface and not more than 25% of the total width of all surfaces |
| 4 | Marked loss of toluidine blue staining with multifocal marked (depth to deep zone) chondrocyte loss and/or collagen disruption or 1 surface with near total loss and partial loss on others, total overall loss less than 50% of width of all surfaces combined |
| 5 | Severe diffuse loss of toluidine blue staining with multifocal severe (depth to tide mark) chondrocyte loss and/or collagen disruption on both femurs and/or tibias, total overall loss greater than 50% of width of all surfaces combined |

TABLE 7

| Score | Ankle Bone Resorption |
| --- | --- |
| 0 | Normal |
| 1 | Minimal - small areas of resorption, not readily apparent on low magnification, rare osteoclasts |
| 2 | Mild - more numerous areas of resorption, not readily apparent on low magnification, osteoclasts more numerous, <¼ of tibia or tarsals at marginal zones resorbed |
| 3 | Moderate - obvious resorption of medullary trabecular and cortical bone without full thickness defects in cortex, loss of some medullary trabeculae, lesion apparent on low magnification, osteoclasts more numerous, ¼ to ⅓ of tibia or tarsals affected at marginal zones |
| 4 | Marked - full thickness defects in cortical bone, often with distortion of profile of remaining cortical surface, marked loss of medullary bone, numerous osteoclasts, ½ to ¾ of tibia or tarsals affected at marginal zones |
| 5 | Severe - Full thickness defects in cortical bone, often with distortion of profile of remaining cortical surface, marked loss of medullary bone, numerous osteoclasts, >¾ of tibia or tarsals affected at marginal zones, severe distortion of overall architecture |

TABLE 8

| Score | Knee Bone Resorption |
| --- | --- |
| 0 | Normal |
| 1 | Minimal - small areas of resorption, not readily apparent on low magnification, approximately 1-10% of total joint width of subchondral bone affected |
| 2 | Mile - more numerous areas of resorption, definite loss of subchondral bone, approximately 11-25% of total joint width of subchondral bone affected |

TABLE 8-continued

Score Knee Bone Resorption

3   Moderate - obvious resorption of subchondral bone, approximately 26-50% of total joint width of subchondral bone affected
4   Marked - obvious resorption of subchondral bone, approximately 51-75% of total joint width of subchondral bone affected
5   Severe - distortion of entire joint due to destruction, approximately 76-100% of total joint width of subchondral bone affected

TABLE 9

Score Periarticular Matrix Deposition

0   Normal
1   Faint, multi-focal metachromatic staining, no excessive expansion of periarticular tissue
2   Darker, diffuse metachromatic staining, no excessive expansion of periarticular tissue
3   Darker, diffuse metachromatic staining, mild expansion of periarticular tissue
4   Darker, diffuse metachromatic staining, moderate expansion of periarticular tissue
5   Darker, diffuse metachromatic staining, severe expansion of periarticular tissue The inflammatory infiltrate in mice and rats with type II collagen arthritis consists of neutrophils and macrophages with smaller numbers of lymphocytes when the lesions are in the acute to subacute phase. Tissue edema and neutrophil exudates within the joint space are common in the acute and subacute phase. As the inflammation progresses to chronic, mononuclear inflammatory cells (monocytes and lymphocytes) predominate and fibroblast proliferation, often with deposition of metachromatic matrix, occurs in synovium and periarticular tissue. Exudate is less common in the joint space.

Clinical data for ankle joint diameter were analyzed by determining the area under the curve (AUC). For calculation of AUC, the daily measurement of ankle joints (using a caliper) for each rat were entered into a spreadsheet, and the area between the treatment days after the onset of disease to the termination day was computed. Means for each group were determined and % inhibition from arthritis controls was calculated by comparing values for treated and normal animals. Data were analyzed using a Student's t-test or Mann-Whitney U test (non-parametric). If applicable, data were analyzed again, across all groups, using a one-way analysis of variance (1-way ANOVA) or Kruskal-Wallis test (non-parametric), along with the appropriate multiple comparison post-test. ANOVA was performed using Prism 5.0c software (GraphPad Software, Inc.). Significance for all tests was set at $p<0.05$. Percent inhibition was calculated using the following formula: % Change=B/A×100, wherein A is the mean normal (mean disease control), and B is the mean treated (mean disease control). The results of the testing are described below in relation to the various, referenced figures. In all cases, n=4 for Normal Controls, and n=10 for the treatment group.

Body weight gain was significantly increased toward normal for treated rats in the following groups as compared to vehicle treated disease controls: 2.5 mg/kg CH-4051 in combination with 0.1 mg/kg MTX—Group 5 (84% increase); 0.2 mg.kg MTX—Group 6 (68% increase), 5 mg/kg CH-4051—Group 7 (84% increase); and 5 mg/kg CH-4051 in combination with 0.2 mg/kg MTX—Group 8 (98% increase). Body weight gain also was significant increased for rats treated with 2.5 mg/kg CH-4051 in combination with 0.1 mg/kg MTX—Group 5 (75% increase) as compared to rats treated with 0.1 mg/kg MTX alone—Group 3. These results are illustrated in FIG. 1.

Daily ankle diameter measurements were significantly reduced toward normal as compared to vehicle controls for rats treated in the following groups: 0.1 mg/kg MTX—Group 3 (significant at day 11); 2.5 mg/kg CH-4051 in combination with 0.1 mg/kg MTX—Group 5 (significant at days 10-17); 5 mg/kg CH-4051—Group 7 (significant at days 10-17); and 5 mg/kg CH-4051 in combination with 0.2 mg/kg MTX—Group 8 (significant at days 10-17). When compared to treatment with MTX alone, daily ankle measurements were also significantly reduced for rats treated with 2.5 mg/kg CH-4051 in combination with 0.1 mg/kg MTX—Group 5 (significant at days 10-17) and 5 mg/kg CH-4051 in combination with 0.2 mg/kg MTX—Group 8 (significant at days 15-17). These results are illustrated in FIG. 2. In FIG. 2, the data line for Group 1 and Group 8 overlap.

Ankle diameter AUC was significantly reduced toward normal as compared to vehicle treated disease controls for rats treated in the following groups: 2.5 mg/kg CH-4051 in combination with 0.1 mg/kg MTX—Group 5 (89% reduction); 0.2 mg/kg MTX—Group 6 (72%); 5 mg/kg CH-4051—Group 7 (81%); and 5 mg/kg CH-4051 in combination with 0.2 mg/kg MTX—Group 8 (100%). Ankle diameter AUC also was significantly reduced as compared to MTX treatment alone for rates treated in the following groups: 2.5 mg/kg CH-4051 in combination with 0.1 mg/kg MTX—Group 5 (85%); and 5 mg/kg CH-4051 in combination with 0.2 mg/kg MTX—Group 8 (100%). These results are illustrated in FIG. 3.

Nine of 10 vehicle treated disease control rats had severe synovitis and periarticular inflammation in at least one and usually both ankle joints with none to moderate pannus and bone resorption, as well as none to marked cartilage damage. All ankle histopathology parameters were significantly reduced toward normal as compared to vehicle treated disease controls for rats treated in the following groups: 2.5 mg/kg CH-4051 in combination with 0.1 mg/kg MTX—Group 5 (81% reduction of summed scores); 0.1 mg/kg MTX—Group 6 (59% reduction of summed scores); 5 mg/kg CH-4051—Group 7 (75% reduction of summed scores), and 5 mg/kg CH-4051 in combination with 0.2 mg/kg MTX—Group 8 (100% reduction of summed scores). All ankle histopathology parameters also were significantly reduced as compare to MTX treatment alone for rats treated with 2.5 mg/kg CH-4051 in combination with 0.1 mg/kg MTX—Group 5 (76% reduction of summed scores). Rats treated with 5 mg/kg CH-4051 in combination with 0.3 mg/kg MTX—Group 8—had significantly reduced ankle inflammation (100% reduction), pannus (100% reduction), and summed scores (100% reduction) as compared to MTX treatment alone. These results are illustrated in FIG. 4 and FIG. 5.

Seven of 10 vehicle treated disease control animals had marked to severe synovitis and periarticular inflammation in at least one knee joint with none to moderate pannus formation, bone resorption, and cartilage damage. All knee histopathology parameters were significantly reduced as compared to vehicle treated disease controls for rates treated in the following groups: 2.5 mg/kg CH-4051 in combination with 0.1 mg/kg MTX—Group 5 (100% reduction of summed scores); 5 mg/kg CH-4051—Group 7 (92% reduction of summed scores), and 5 mg/kg CH-4051 in combination with 0.2 mg/kg MTX—Group 8 (100% reduction of summed scores). Rats treated with 0.2 mg/kg MTX—Group 6—had significantly reduced knee pannus (91% reduction), cartilage damage (91% reduction), and bone resorption (95% reduction) as compared to vehicle controls. All knee histopathology parameters also were significantly reduced as compared to MTX treatment alone for rats treated with 2.5 mg/kg CH-4051 in combination with 0.1 mg/kg MTX—Group 5 (100% reduction). Two of 10 rats treated with 5 mg/kg CH-4051 in combination with 0.2 mg/kg MTX—Group 8—had minimal to mild bone marrow hypocellularity. These results are illustrated in FIG. 6 and FIG. 7.

Representative photomicrographs of ankles with the approximate mean score for each group are provided in FIG. 8 through FIG. 15. Representative photomicrographs of knees with the highest score/most severe lesions for each group as provided in FIG. 16 through FIG. 23.

The results of the above-described study demonstrate that treatment with 2.5 mg/kg CH-4051 (daily doses) or 0.1 mg/kg MTX (dosed 2 times per week) had only minimal, non-significant effects on developing arthritis parameters. Treatment with the combination of 2.5 mg/kg CH-4051 (daily doses) and 0.1 mg/kg MTX (dosed 2 times per week) (i.e., Group 5), however, provided synergistic effects resulting in statistically significant benefit on all parameters. Rats given this combination treatment were clinically normal with the exception of a few joints with minor swelling. Treatment with CH-4051 alone or MTX alone at higher doses (i.e., 5 mg/kg CH-4051 per day or 0.2 mg/kg MTX twice weekly) resulted in good inhibition of all arthritis parameters; however, the combination treatment at these higher doses (i.e., Group 8) provided complete elimination of all disease symptoms. Overall, the above-described test results indicate that low doses of CH-4051 and MTX result in synergistic effects in treating developing type II collagen arthritis in rats.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for treating a subject suffering from an arthritis related condition, the method comprising administering to the subject a first compound according to a first dosing schedule and a second compound according to a second, different dosing schedule, wherein the first compound is methotrexate or a derivative thereof and the second compound is an antifolate compound according to Formula (6):

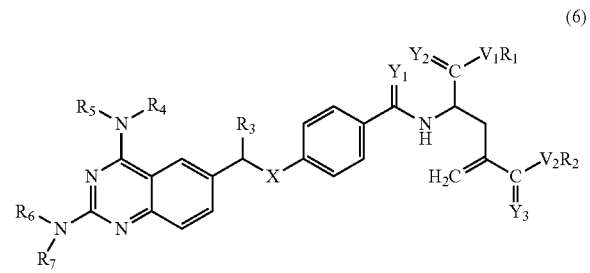

(6)

wherein:
X is $CHR_8$ or $NR_8$;
$Y_1$, $Y_2$, and $Y_3$ independently are O or S;
$V_1$ and $V_2$ independently are O, S, or NZ;

Z is H, optionally substituted alkyl, optionally substituted alkenyl, optionally substituted alkynyl, or alkaryl;

$R_1$ and $R_2$ independently are H, optionally substituted alkyl, optionally substituted alkenyl, optionally substituted alkynyl, or alkaryl;

$R_3$ is H, optionally substituted alkyl, optionally substituted alkenyl, optionally substituted alkynyl, optionally substituted alkoxy, hydroxyl, or halo; and $R_4$, $R_5$, $R_6$, $R_7$, and $R_8$ independently are H, optionally substituted alkyl, optionally substituted alkenyl, optionally substituted alkynyl, acyl, —C(O)-alkyl, —C(O)-alkenyl, or —C(O)-alkynyl; or a pharmaceutically acceptable ester, amide, salt, solvate, enantiomer, or prodrug thereof; and wherein the first compound and the second compound are administered in amounts sufficient to provide a synergistic effect in treating the arthritis related condition.

2. The method of claim 1, wherein the first dosing schedule comprises administering the first compound once per week.

3. The method of claim 1, wherein the first dosing schedule comprises administering the first compound twice per week.

4. The method of claim 1, wherein the second dosing schedule comprises administering the second compound at least three times per week.

5. The method of claim 1, wherein the second dosing schedule comprises administering the second compound at least once per day.

6. The method of claim 4, wherein the second dosing schedule comprises administering the second compound at least twice per day.

7. The method of claim 1, wherein the second compound is an antifolate compound according to formula (7):

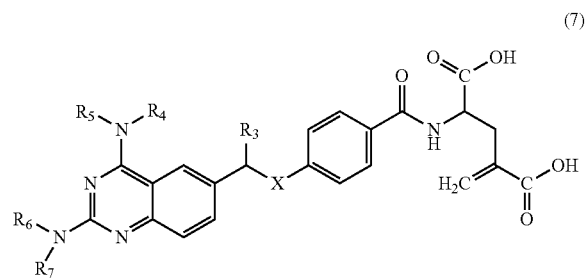

(7)

wherein:
X is $CHR_8$ or $NR_8$;

$R_3$ is H, optionally substituted alkyl, optionally substituted alkenyl, optionally substituted alkynyl, optionally substituted alkoxy, hydroxyl, or halo; and $R_4$, $R_5$, $R_6$, $R_7$, and $R_8$ independently are H, optionally substituted alkyl, optionally substituted alkenyl, optionally substituted alkynyl, acyl, —C(O)-alkyl, —C(O)-alkenyl, or —C(O)-alkynyl; or a pharmaceutically acceptable ester, amide, salt, solvate, enantiomer, or prodrug thereof.

8. The method of claim 1, wherein the second compound is an antifolate compound according to Formula (9):

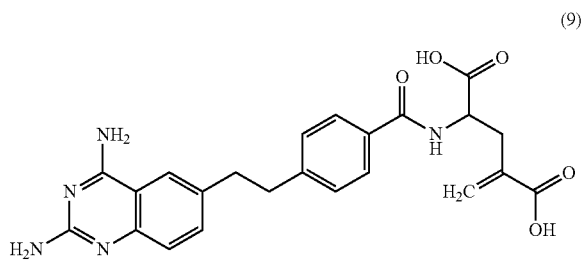 [SMILES: C=C(CC(NC(=O)c1ccc(CCc2ccc3nc(N)nc(N)c3c2)cc1)C(=O)O)C(=O)O]

(9)

or a pharmaceutically acceptable ester, amide, salt, solvate, enantiomer, or prodrug thereof.

9. The method of claim 1, wherein the second compound is an antifolate compound according to Formula (II):

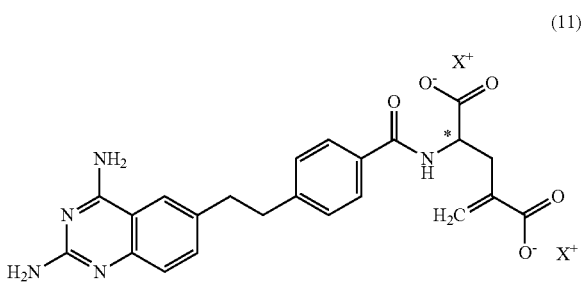

(11)

or an enantiomer thereof, wherein each $X^+$ independently is a salt-forming counterion.

10. The method of claim 9, wherein $X^+$ is an alkali metal cation.

11. The method of claim 9, wherein $X^+$ is sodium.

12. The method of claim 9, wherein $X^+$ is potassium.

13. The method of claim 9, wherein the antifolate compound is a crystalline salt.

14. The method of claim 9, wherein the antifolate compound is a racemic salt.

15. The method of claim 9, wherein the second compound is an antifolate compound according to Formula (12):

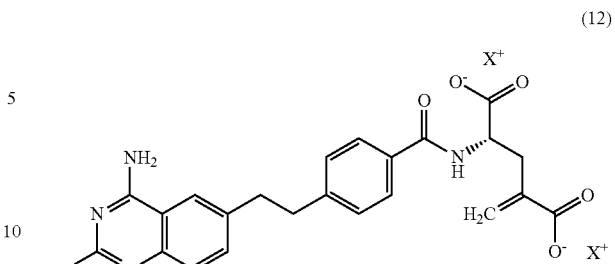

(12)

wherein each $X^+$ independently is a salt-forming counterion, and wherein the antifolate compound is in the (S) enantiomeric form.

16. The method of claim 15, wherein the antifolate compound exhibits an enantiomeric purity for the (S) enantiomer of at least about 90%.

17. The method of claim 15, wherein the antifolate compound exhibits an enantiomeric purity for the (S) enantiomer of at least about 95%.

18. The method of claim 15, wherein the antifolate compound exhibits an enantiomeric purity for the (S) enantiomer of at least about 99%.

19. The method of claim 15, wherein the second compound is an antifolate compound according to Formula (12) that is a crystalline, disodium salt in the (S) enantiomeric form exhibiting an enantiomeric purity for the (S) enantiomer of at least about 99%.

20. The method of claim 15, wherein the second compound is an antifolate compound according to Formula (12) that is a crystalline, dipotassium salt in the (S) enantiomeric form exhibiting an enantiomeric purity for the (S) enantiomer of at least about 99%.

21. The method of claim 1, wherein the condition is selected from the group consisting of rheumatoid arthritis, spondyloarthropaties (ankylosing spondylitis), osteoarthritis, arthritis associated with acute gout, arthritis associated with chronic gout, and arthritis associated with systemic lupus erythematosus.

22. The method of claim 21, wherein the condition is rheumatoid arthritis.

* * * * *

UNITED STATES PATENT AND TRADEMARK OFFICE
CERTIFICATE OF CORRECTION

PATENT NO. : 8,658,652 B2
APPLICATION NO. : 13/313116
DATED : February 25, 2014
INVENTOR(S) : Michael J. Roberts and Gerry Rowse It is certified that error appears in the above-identified patent and that said Letters Patent is hereby corrected as shown below:

In the Specification

In Columns 23-24, under the heading "Step 4", the chemical structure, specifically, Formula I-04, was incorrectly labeled. The correct chemical structure, as shown on page 31 of the original specification submitted to the USPTO on December 7, 2011 is as follows:

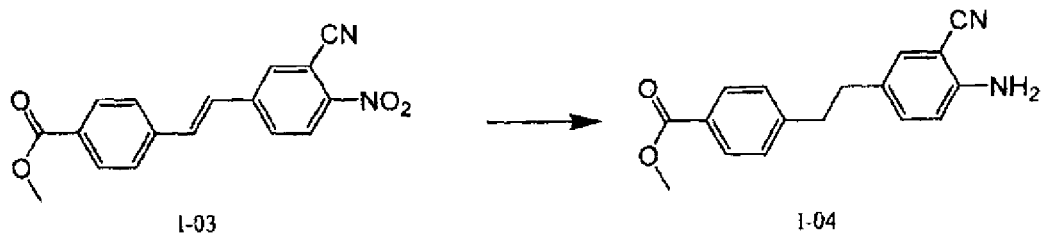

In the Claims

In Column 47, Claim 9, Line 16, reference is made to "Formula (II):"

It should read "Formula (11):"

Signed and Sealed this
Eighth Day of July, 2014

Michelle K. Lee
*Deputy Director of the United States Patent and Trademark Office*